(12) United States Patent
Yoshida et al.

(10) Patent No.: US 10,980,416 B2
(45) Date of Patent: Apr. 20, 2021

(54) BLOOD FLOW MEASUREMENT APPARATUS

(71) Applicants: National University Corporation ASAHIKAWA MEDICAL UNIVERSITY, Asahikawa (JP); KABUSHIKI KAISHA TOPCON, Itabashi-ku (JP)

(72) Inventors: Akitoshi Yoshida, Asahikawa (JP); Masahiro Akiba, Toda (JP)

(73) Assignees: National University Corporation ASAHIKAWA MEDICAL UNIVERSITY, Asahikawa (JP); KABUSHIKI KAISHA TOPCON, Itabashi-ku (JP)

( * ) Notice: Subject to any disclaimer, the term of this patent is extended or adjusted under 35 U.S.C. 154(b) by 318 days.

(21) Appl. No.: 15/531,842

(22) PCT Filed: Nov. 2, 2015

(86) PCT No.: PCT/JP2015/080970
§ 371 (c)(1),
(2) Date: May 31, 2017

(87) PCT Pub. No.: WO2016/098474
PCT Pub. Date: Jun. 23, 2016

(65) Prior Publication Data
US 2018/0279874 A1 Oct. 4, 2018

(30) Foreign Application Priority Data
Dec. 19, 2014 (JP) .............................. JP2014-257035

(51) Int. Cl.
*A61B 3/12* (2006.01)
*G01N 21/17* (2006.01)
(Continued)

(52) U.S. Cl.
CPC .......... *A61B 3/1233* (2013.01); *A61B 3/0025* (2013.01); *A61B 3/10* (2013.01);
(Continued)

(58) Field of Classification Search
CPC ..... A61B 3/1233; A61B 3/1241; A61B 3/102; A61B 3/12
See application file for complete search history.

(56) References Cited

U.S. PATENT DOCUMENTS

| 2009/0005691 A1 | 1/2009 | Huang et al. |
| 2009/0073387 A1 * | 3/2009 | Meyer ...................... A61B 3/12 351/246 |

(Continued)

FOREIGN PATENT DOCUMENTS

| JP | 2007-319403 A | 12/2007 |
| JP | 2009-106532 A | 5/2009 |

(Continued)

OTHER PUBLICATIONS

International Search Report dated Feb. 2, 2016, in PCT/JP2015/080970, filed Nov. 2, 2015.

(Continued)

*Primary Examiner* — Hien N Nguyen
(74) *Attorney, Agent, or Firm* — Oblon, McClelland, Maier & Neustadt, L.L.P.

(57) ABSTRACT

A blood flow measurement apparatus of an embodiment includes an image acquisition unit, an image region specification unit, a measurement location setting unit, a scanner, and a blood flow information generation unit. The image acquisition unit acquires an image of a living body. The image region specification unit analyzes the image to specify a plurality of blood vessel regions. The measurement location setting unit sets a plurality of measurement locations that intersects with the plurality of blood vessel regions. The (Continued)

scanner scans a plurality of cross sections of the living body corresponding to the plurality of measurement locations using optical coherence tomography. The blood flow information generation unit generates blood flow information on the living body based on data acquired through the scan.

10 Claims, 11 Drawing Sheets

(51) Int. Cl.
    *A61B 3/10*     (2006.01)
    *A61B 5/026*     (2006.01)
    *A61B 5/00*     (2006.01)
    *A61B 3/00*     (2006.01)

(52) U.S. Cl.
    CPC .............. *A61B 3/102* (2013.01); *A61B 3/12* (2013.01); *A61B 3/1241* (2013.01); *A61B 5/0066* (2013.01); *A61B 5/026* (2013.01); *G01N 21/17* (2013.01); *A61B 5/489* (2013.01)

(56) References Cited

U.S. PATENT DOCUMENTS

| | | |
|---|---|---|
| 2012/0218517 A1 | 8/2012 | Imamura |
| 2014/0063458 A1 | 3/2014 | Imamura |
| 2014/0073917 A1 | 3/2014 | Huang et al. |
| 2014/0204342 A1* | 7/2014 | Higuchi ................ A61B 3/14 351/208 |
| 2015/0313466 A1 | 11/2015 | Yoshida |
| 2016/0302738 A1 | 10/2016 | Yoshida et al. |
| 2016/0310024 A1 | 10/2016 | Yoshida et al. |

FOREIGN PATENT DOCUMENTS

| | | | |
|---|---|---|---|
| JP | 2009-165710 A | | 7/2009 |
| JP | 2009165710 | * | 7/2009 |
| JP | 2010-523286 A | | 7/2010 |
| JP | 2010523286 | * | 7/2010 |
| JP | 2012-115572 A | | 6/2012 |
| JP | 2012-176095 A | | 9/2012 |
| JP | 2013-184018 A | | 9/2013 |
| JP | 2013-202298 A | | 10/2013 |
| JP | 2013-208158 A | | 10/2013 |
| JP | 2013208158 | * | 10/2013 |
| JP | 2014-140474 A | | 8/2014 |

OTHER PUBLICATIONS

Office Action dated Oct. 1, 2019 in Japanese Patent Application No. 2018-229545 (with unedited computer generated English translation), 10 pages.

* cited by examiner

BLOOD FLOW MEASUREMENT APPARATUS

FIELD

Embodiments described herein relate generally to a blood flow measurement apparatus.

BACKGROUND

Optical coherence tomography (OCT) is utilized not only for morphology measurement of an object but also for function measurement. For example, OCT apparatuses for blood flow measurement of living bodies are known. The blood flow measurement using OCT is applied to blood vessels of the eye fundus.

[Patent Document 1] Japanese Unexamined Patent Application Publication No. 2013-184018
[Patent Document 2] Japanese Unexamined Patent Application Publication No. 2009-165710
[Patent Document 3] Japanese Unexamined Patent Application Publication (Translation of PCT Application) No. 2010-523286

In blood flow measurement, from data acquired through iteratively scanning a cross section that intersects a blood vessel, a phase image that represents a chronological change in phase difference in the cross section is formed. In order to obtain a suitable phase image, it is necessary that the intervals of the scan points (A scans) for scanning the cross section are sufficiently dense and that the iteration rate of the scan is sufficiently fast (for example, sampling intervals during one heartbeat period are sufficiently dense).

Such a dense and fast scan limits the width of the cross section. Therefore, it is difficult to perform the measurements of the blood flow for a plurality of blood vessels with a single scan (in particular, it is difficult to perform the measurements of the blood flow for a plurality of widely distributed blood vessels with a single scan). For example, in the blood flow measurement of the fundus, there is a restriction on the amount of light that can be applied to the subject's eye. Therefore, the enlargement of the width of the cross section is substantially impossible, and such a problem becomes big.

On the other hand, there is a desire to measure blood flow for a plurality of blood vessels (that are widely distributed). For example, there are cases where it is desired to measure the blood flow for a plurality of blood vessels distributed around the optic nerve head in order to grasp the overall blood flow state in the fundus. In such a case, it is conceivable to iteratively perform circle scan around the optic nerve head. However, considering the length of the path of the circle scan (i.e., the width of the cross section), the achievement of both the dense scan interval and the high iteration rate is difficult.

SUMMARY

The purpose of an embodiment is to provide a technique capable of performing blood flow measurement of a plurality of blood vessels in a suitable manner.

A blood flow measurement apparatus of an embodiment includes: an image acquisition unit configured to acquire an image of a living body; an image region specification unit configured to analyze the image to specify a plurality of blood vessel regions; a measurement location setting unit configured to set a plurality of measurement locations that intersects with the plurality of blood vessel regions; a scanner configured to scan a plurality of cross sections of the living body corresponding to the plurality of measurement locations using optical coherence tomography; and a blood flow information generation unit configured to generate blood flow information on the living body based on data acquired through the scan.

According to the embodiment, the blood flow measurement of the plurality of blood vessels can be performed in a suitable manner.

DETAILED DESCRIPTION

Figure 1:
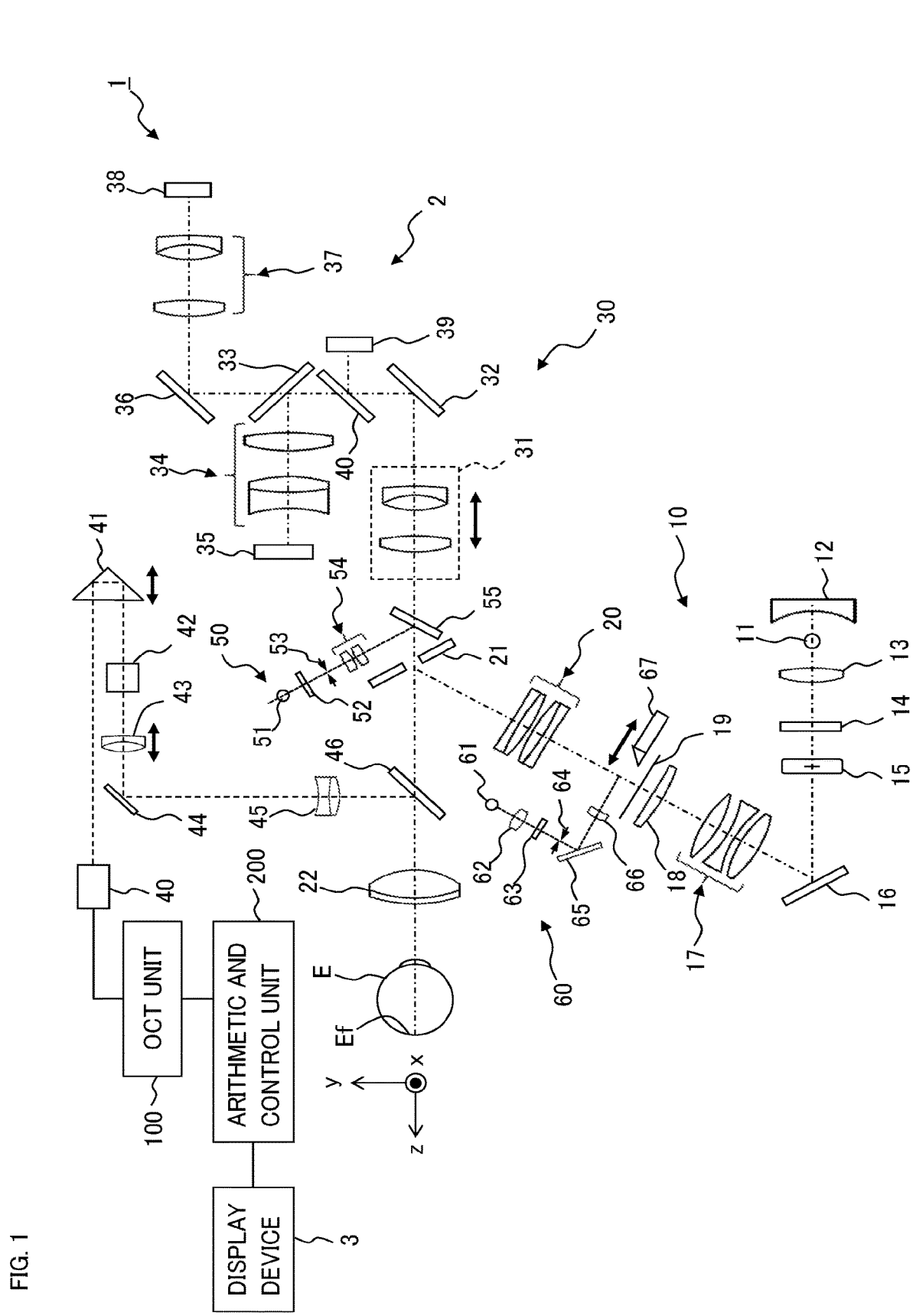
FIG. 1 is a schematic diagram illustrating an example of the configuration of the blood flow measurement apparatus according to the embodiment.

Exemplary embodiments of the present invention will be described in detail with referring to the drawings. Any of the contents of the documents cited in the present specification may be applied to the embodiments below.

A blood flow measurement apparatus of an embodiment acquires information on the blood flow of a living body using OCT. The blood flow measurement apparatus is capable of acquiring images of the living body using OCT. Described below is the case in which Fourier domain OCT (in particular, spectral domain OCT) is utilized to perform the blood flow measurement for eye fundus. The object of blood flow measurement is not necessarily eye fundus. The object of blood flow measurement may be any biological tissue such as skin or internal organs. The type of OCT is not limited to spectral domain OCT. Any type of OCT such as swept source OCT or time domain OCT may be utilized. The embodiment below describes an apparatus that is a combination of an OCT apparatus and a fundus camera. Similar configurations to the embodiment below may be applied to other type such as an apparatus configured as a combination of an OCT apparatus and a slit lamp microscope, or a combination of an OCT apparatus and an ophthalmic operational microscope. Similar configurations to the embodiment below may also be applied to an apparatus having the OCT function only.

<Configuration>

As shown in FIG. 1, the blood flow measurement apparatus 1 includes the fundus camera unit 2, the OCT unit 100, and the arithmetic and control unit 200. The fundus camera unit 2 has a configuration for photographing the fundus Ef. The OCT unit 100 has a configuration for acquiring OCT images of the fundus Ef. The arithmetic and control unit 200 has a configuration for executing various kinds of calculation and control.

<Fundus Camera Unit>

The fundus camera unit 2 acquires two dimensional images rendering the surface morphology of the fundus Ef (referred to as fundus images). The kinds of the fundus images include observation images and photographed images. An observation image is a monochrome image acquired at a preset frame rate using near infrared light. The kinds of the photographed images include: color images captured using visible flash light; monochrome images captured using near infrared light or visible light (e.g., fluorescence images such as fluorescein angiograms, indocyanine green angiograms, autofluorescence images).

The fundus camera unit 2 includes the illumination optical system 10 and the photographing optical system 30. The illumination optical system 10 irradiates the eye E with illumination light. The photographing optical system 30 receives return light (e.g., fundus reflection light, cornea reflection light, fluorescence, etc.) of the illumination light from the eye E. The fundus camera unit 2 guides measurement light from the OCT unit 100 toward the eye E, and guides return light of the measurement light from the eye E to the OCT unit 100.

Light emitted from the observation light source 11 in the illumination optical system 10 (i.e., observation illumination light) is reflected by the reflection mirror 12 having the curved reflective surface, is refracted by the condenser lens 13, and passes through the visible light cut filter 14. Thereby, the observation illumination light becomes near infrared light. Then, the observation illumination light once converges at a point near the photographing light source 15, is reflected by the mirror 16, passes through the relay lenses 17 and 18, the diaphragm 19, and relay lens 20, is reflected by the peripheral area (that is, the area surrounding the aperture) of the aperture mirror 21, passes through the dichroic mirror 46, is refracted by the objective lens 22, and is projected onto the eye E.

Return light of the observation illumination light from the eye E is refracted by the objective lens 22, passes through the dichroic mirror 46, passes through the aperture formed in the central area of the aperture mirror 21, passes through the dichroic mirror 55, passes through the focusing lens 31, is reflected by the mirror 32, passes through the half mirror 40, is reflected by the dichroic mirror 33, and converges on the light receiving surface of the area sensor 35 with the condenser lens 34. The area sensor 35 detects the return light at a preset frame rate. With this, an observation image of the fundus Ef, an observation image of the anterior segment or the like is acquired.

Light emitted from the photographing light source 15 (i.e., photographing illumination light) is guided along the same route as that of the observation illumination light, and projected onto the eye E (that is, onto the fundus Ef). Return light (e.g., fundus reflection light, fluorescence, etc.) of the photographing illumination light is also guided along the same route as that of the observation illumination light until the dichroic mirror 33, passes through the dichroic mirror 33, is reflected by the mirror 36, and converges on the light receiving surface of the area sensor 38 with the condenser lens 37. With this, a photographed image of the fundus Ef or the like is acquired.

The liquid crystal display (LCD) 39 displays a fixation target, an optotype (visual acuity chart), and the like. Part of light output from the LCD 39 is reflected by the half mirror 40, is reflected by the mirror 32, passes through the focusing lens 31 and the dichroic mirror 55, passes through the aperture of the aperture mirror 21, passes through the dichroic mirror 46, is refracted by the objective lens 22, and is projected onto the eye (that is, onto the fundus Ef). The fixation position of the eye E is changed by changing the displayed position of the fixation target on the LCD 39.

The fundus camera unit 2 includes the alignment optical system 50 and the focus optical system 60. The alignment optical system 50 generates an indicator for position adjustment of the optical system of the apparatus with respect to the eye E. Such position adjustment is referred to as alignment, and the indicator for the alignment is referred to as the alignment indicator. The focus optical system 60 generates an indicator for focus adjustment with respect to the eye E. The indicator for the focus adjustment is referred to as the split indicator.

Near infrared light emitted from the light emitting diode (LED) 51 in the alignment optical system 50 (referred to as alignment light) passes through the diaphragms 52 and 53 and the relay lens 54, is reflected by the dichroic mirror 55, passes through the aperture of the aperture mirror 21, passes through the dichroic mirror 46, and is projected onto the eye E (i.e., the cornea) with the objective lens 22. Return light of the alignment light is guided along the same route as that of the return light of the observation illumination light, and detected by the area sensor 35. The image detected by the area sensor 35 (referred to as an alignment indicator image) is rendered in the observation image. The user or the arithmetic and control unit 200 can perform alignment based on the position of the alignment indicator image in the same manner as with conventional fundus cameras.

When performing focus adjustment, the reflective surface of the reflection rod 67 is placed in the optical path of the illumination optical system 10 in an inclined manner. Near infrared light emitted from the LED 61 in the focus optical system 60 (referred to as focus light) passes through the relay lens 62, is split into two light beams with the split indicator plate 63, passes through the two-aperture diaphragm 64, is reflected by the mirror 65, once converges on the reflective surface of the reflection rod 67 with the condenser lens 66, is reflected by the reflection rod 67, passes through the relay lens 20, is reflected by the aperture mirror 21, passes through the dichroic mirror 46, is refracted by the objective lens 22, and is projected onto the eye E (i.e., the fundus Ef). Return light of the focus light is guided along the same route as that of the return light of the alignment light, and detected by the area sensor 35. The image detected by the area sensor 35 (referred to as a split indicator image) is rendered in the observation image. The user or the arithmetic and control unit 200 can perform focus adjustment by moving the focusing lens 31 and the focus optical system 60 based on the position of the split indicator image in the same manner as with conventional fundus cameras.

Figure 3:
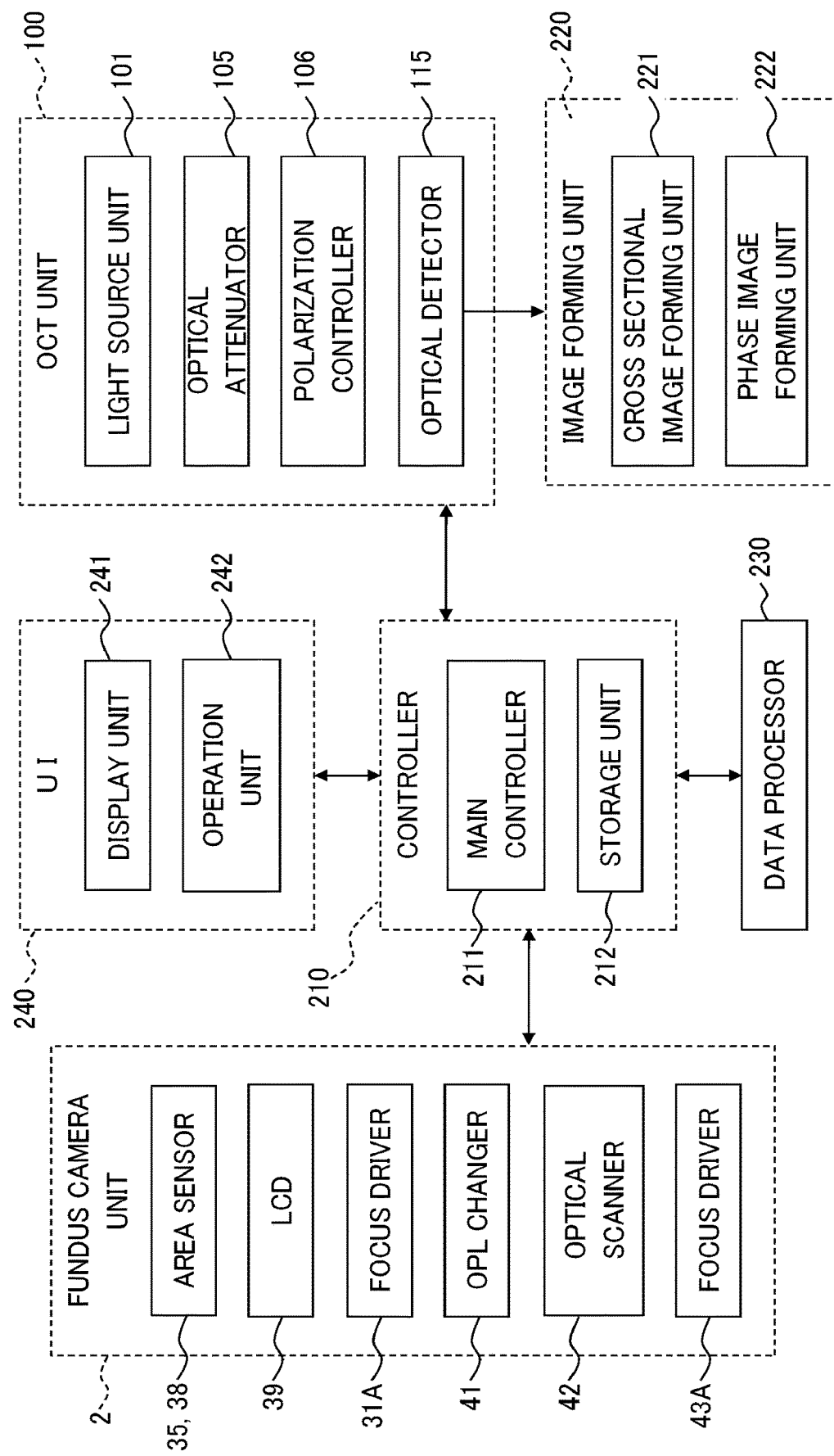
FIG. 3 is a schematic diagram illustrating an example of the configuration of the blood flow measurement apparatus according to the embodiment.

The focus driver 31A shown in FIG. 3 moves the focusing lens 31, and a driver mechanism (not illustrated) moves the focus optical system 60.

After the completion of alignment (and focus adjustment), tracking may be performed. Tracking is an operation for moving the optical system of the apparatus in accordance with the movement of the eye E.

The dichroic mirror 46 couples the optical path for fundus photography and the optical path for OCT together. The optical path for OCT is referred to as a measurement arm, sample arm, or the like. The dichroic mirror is designed to reflect light of wavelength bands for OCT and to transmit light for fundus photography. Listed from the OCT unit 100 side, the collimator lens unit 40, the optical path length (OPL) changer 41, the optical scanner 42, the focusing lens 43, the mirror 44, and the relay lens 45 are placed in the optical path for OCT The optical path length changer 41 changes the length of the measurement arm. The optical path length changer 41 includes, for example, a corner cube movable in the direction shown by the arrow in the FIG. 1. Change of the optical path length of the measurement arm may be utilized for the adjustment of the optical path length according to the axial length of the eye E, the adjustment of the interference state, or the like.

The optical scanner 42 has a configuration capable of two-dimensionally deflecting light guided along the measurement arm (i.e., the measurement light LS). In an example, the optical scanner 42 is configured to be capable of deflecting the measurement light LS in mutually orthogonal directions (e.g., the x direction and the y direction). With such a configuration, various types of scan patterns can be realized. When a configuration for anterior segment OCT (e.g., an attachment including a lens system) is employed, the anterior segment of the eye E is scanned with the measurement light LS. The optical scanner 42 includes, for example, a Galvano mirror, micro electro mechanical systems (MEMS) mirror, resonant mirror, or the like.

<OCT Unit>

Figure 2:
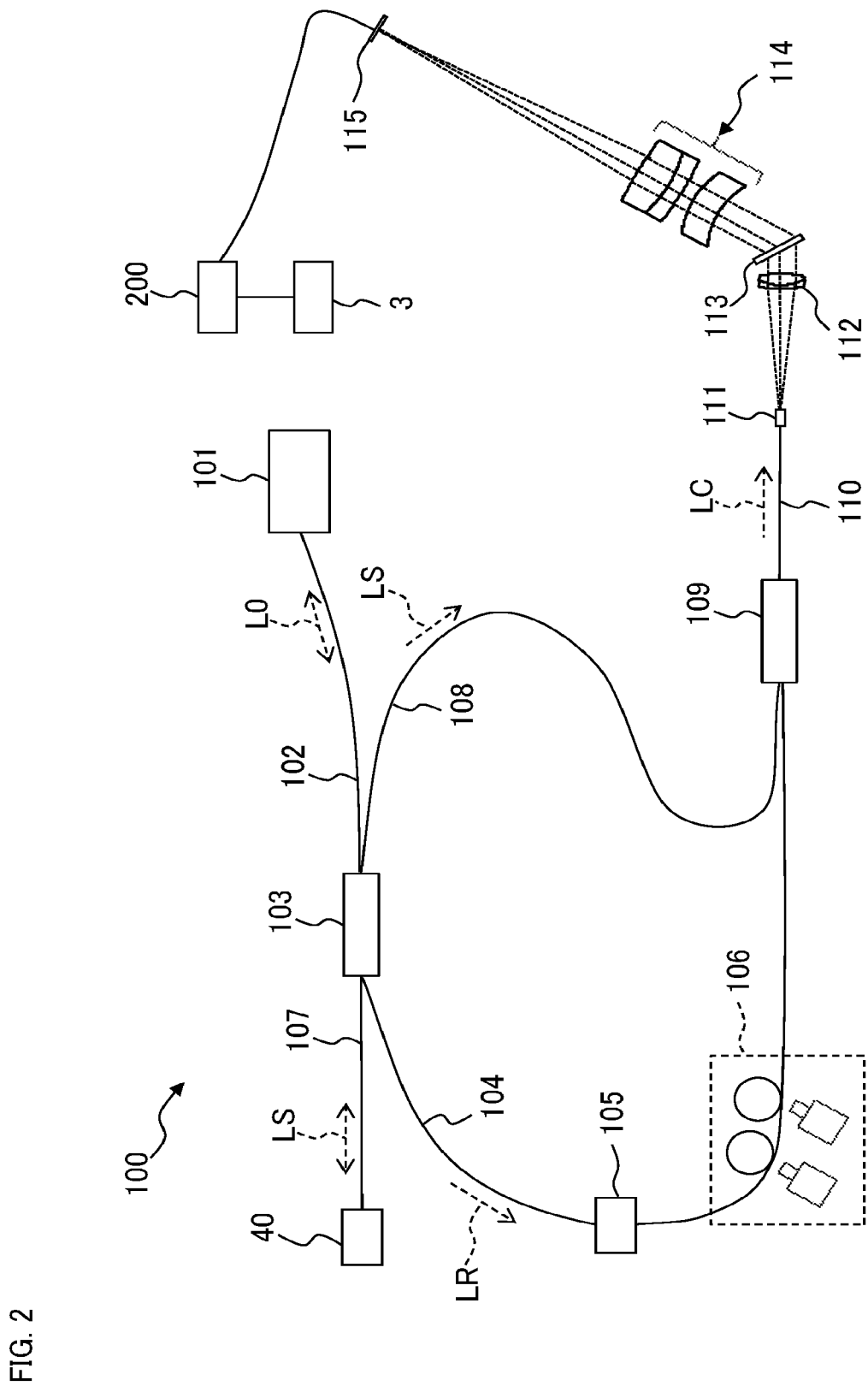
FIG. 2 is a schematic diagram illustrating an example of the configuration of the blood flow measurement apparatus according to the embodiment.

FIG. 2 shows a configuration example of the OCT unit 100. The configuration of the OCT unit 100 depends on the type of OCT applied. The configuration shown in FIG. 2 is an example for spectral domain OCT. The spectral domain OCT system, in general, includes a low coherence light source and a spectrometer. On the other hand, the swept source OCT system includes, for example, a wavelength tunable light source and a balanced photo diode.

In the spectral domain OCT system, the light L0 emitted from the light source unit 101 is broadband, low coherence light. In an example, the light L0 may include near infrared wavelength bands (e.g., about 800 nm to 900 nm), and the temporal coherence length of the light L0 may be about several tens μm. Alternatively, the light L0 may be near infrared light having the central wavelength of about 1040 nm to 1060 nm. The light source unit 101 includes a light emitting device such as a super luminescent diode (SLD), an LED, or a semiconductor optical amplifier (SOA).

The light L0 output from the light source unit 101 is guided to the fiber coupler 103 through the optical fiber 102, and is split into the measurement light LS and the reference light LR.

The reference light LR is guided to the optical attenuator 105 through the optical fiber 104. Under the control of the arithmetic and control unit 200, the optical attenuator 105 automatically adjusts the amount of the reference light LR guided through the optical fiber 104 as with conventional techniques. The reference light LR, the amount of which has been adjusted by the optical attenuator 105, is guided to the polarization controller 106 through the optical fiber 104. Under the control of the arithmetic and control unit 200, the polarization controller 106 controls the polarization state of the reference light LR guided through the optical fiber 104 as with conventional techniques. The reference light LR, the polarization state of which has been adjusted, is guided to the fiber coupler 109.

The measurement light LS generated by the fiber coupler 103 is guided through the optical fiber 107, and is converted to a parallel light beam with the collimator lens unit 40. Then, the measurement light LS passes through the optical path length changer 41, the optical scanner 42, the focusing lens 43, the mirror 44, and the relay lens 45, is reflected by the dichroic mirror 46, is refracted by the objective lens 22, and is projected onto the eye E (that is, onto the fundus Ef). The measurement light LS is scattered and reflected at various depth positions of the fundus Ef. Return light of the measurement light LS (e.g., backscattering light, reflection light, fluorescence) travels along the same route as the outward way in the opposite direction, is guided to the fiber coupler 103, and is guided to the fiber coupler 109 through the optical fiber 108. The focusing lens 43 is moved by the focus driver 43A shown in FIG. 3.

The fiber coupler 109 superposes the return light of the measurement light LS and the reference light LR that has traveled through the optical fiber 104. The interference light LC generated by the superposition is guided through the optical fiber 110, exits from the exit end 111 of the optical fiber 110, is converted to a parallel light beam with the collimator lens 112, is split into spectra with the diffraction grating 113, converges with the condenser lens 114, and is projected on the light receiving surface of the optical detector 115. The optical detector 115 is, for example, a line sensor, and detects the respective spectral components of the interference light LC split into spectra and generates an electric signal (that is, a detection signal). The detection signal generated is sent to the arithmetic and control unit 200.

<Arithmetic and Control Unit>

The arithmetic and control unit 200 executes control of the fundus camera 2, the display device 3, and the OCT unit 100, various kinds of calculation processing, formation of OCT images, etc. The arithmetic and control unit 200 includes a user interface such as a display device, an input device, an operation device. The description of the configuration of the arithmetic and control unit 200 will be given in the description of the control system below.

<Control System>

Figure 4:
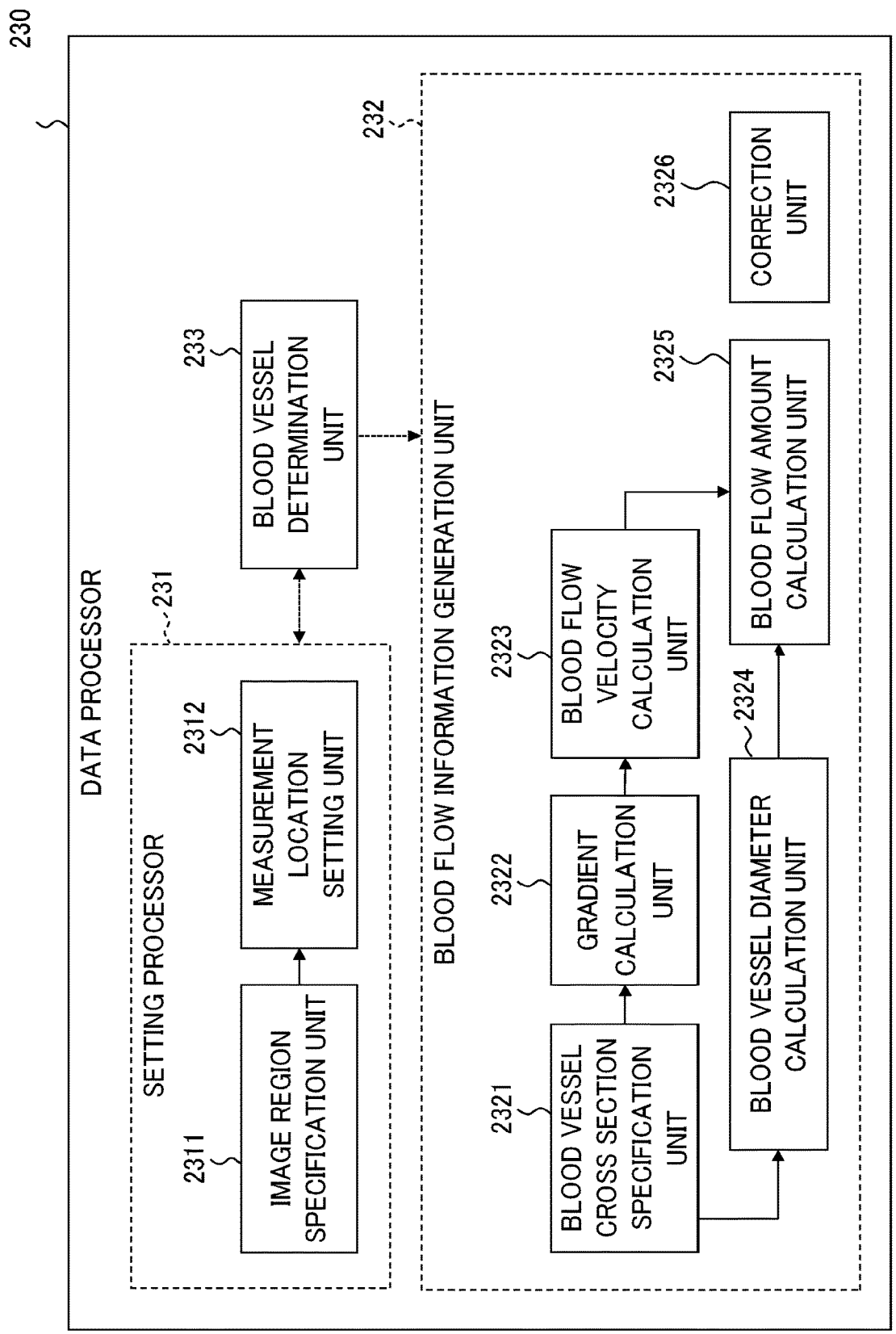
FIG. 4 is a schematic diagram illustrating an example of the configuration of the blood flow measurement apparatus according to the embodiment.

The control system of the blood flow measurement apparatus 1 will be described with referring to FIGS. 3 and 4.

(Controller)

The controller 210 is the center of the control system of the blood flow measurement apparatus 1. The controller 210 includes the main controller 211 and the storage unit 212.

(Main Controller)

The main controller 211 executes control of the fundus camera 2, the OCT unit 100, and the arithmetic and control unit 200. The main controller 211 stores data in the storage unit 212 and reads out data from the storage unit 212.

(Storage Unit)

The storage unit 212 stores various kinds of data. Examples of data stored in the storage unit 212 include, for example, OCT images, fundus images, and subject's eye information. The subject's eye information is information on subject's eyes and/or subjects, and includes input information such as patient IDs, medical information such as electronic medical records, or the like. The storage unit 212 stores computer programs and data for operating the blood flow measurement apparatus 1.

(Image Forming Unit)

The image forming unit 220 forms image data of a cross sectional image and image data of a phase image based on detection signals from the optical detector 115. The image data will be described later. Sometimes, the present specification does not make distinction between "image data" and an "image" created based on the image data. The image forming unit 220 includes the cross sectional image forming unit 221 and the phase image forming unit 222.

In the present embodiment, two different kinds of scans (first scan and second scan) are applied to the fundus Ef. In the first scan, a first cross section that intersects a predetermined interested blood vessel of the fundus Ef is repeatedly scanned with the measurement light LS. In the second scan, a second cross section that intersects with the interested blood vessel is scanned with the measurement light LS. The second cross section is set near the first cross section. It may be desirable that the first cross section and the second cross section are oriented in such a manner that they are orthogonal to the direction of the course of the interested blood vessel.

Figure 5:
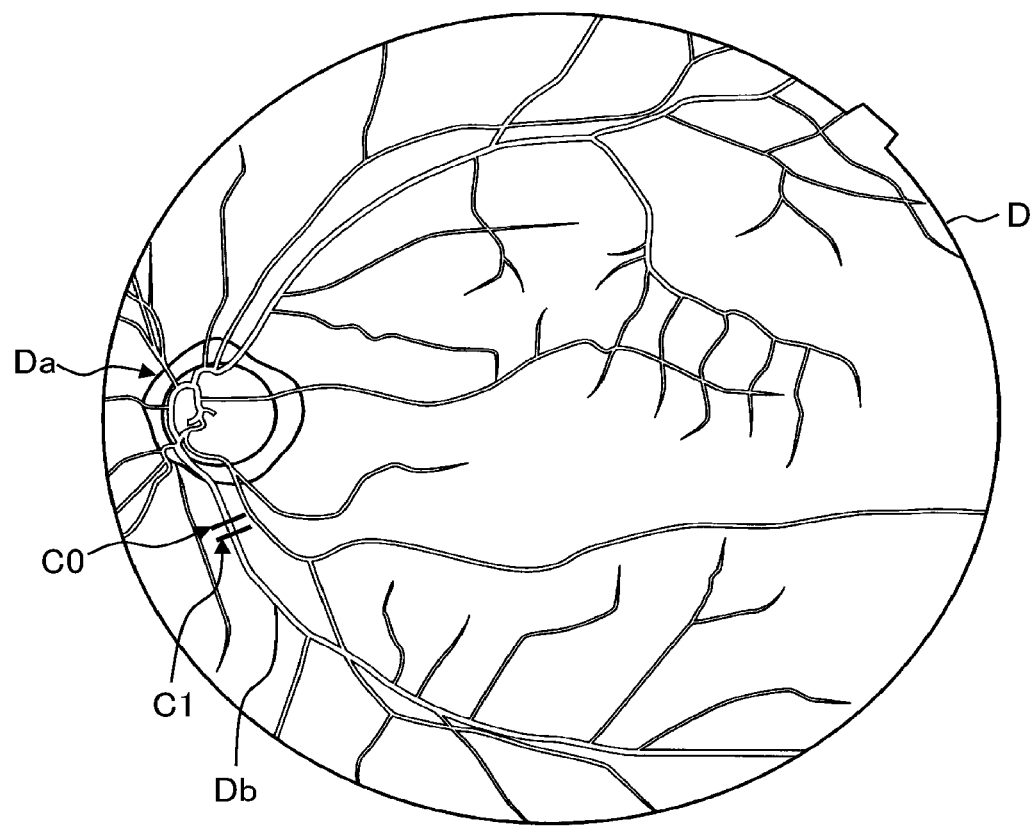
FIG. 5 is a schematic diagram illustrating an example of the operation of the blood flow measurement apparatus according to the embodiment.

FIG. 5 shows a specific example of the first cross section and the second cross section. On the fundus image D shown in FIG. 5, the first cross section C0 and the second cross section C1 are illustrated. The first cross section C0 and the second cross section C1 are set near the optic nerve head Da of the fundus Ef. The first cross section C0 and the second cross section C1 are set in such a manner that both of them intersect the predetermined interested blood vessel Db. The second cross section C1 may be set more on upstream side of the interested blood vessel Db than the first cross section C0, or may be set more on downstream side. Further, the second cross section may include two or more cross sections.

It may be desirable that the first cross section and the second cross section are performed during a period equal to or longer than one heartbeat (i.e., one pulsation cycle, or cardiac cycle) of the heart of the patient. With this, blood flow information is acquired for all time phases of the cardiac cycle. The execution period of the first scan may be a preset period with a constant length, or may be set for each patient or each examination. In the former case, it is possible to set a period shorter than that with a conventional technique. For example, conventionally, a period sufficiently longer than the cardiac cycle (e.g., 2 seconds) is applied in order to securely acquire data over one cardiac cycle. On the other hand, in the present embodiment, for example, by employing the configuration of detecting a predetermined time phase through monitoring the chronological change in the phase difference represented by the phase image and of starting data acquisition from the time phase, it becomes possible to apply the period equal to the cardiac cycle (e.g., 1 second) or slightly longer period than cardiac cycle. In the latter case, examination data such as an electro cardiogram of the patient can be referred to. Here, any kinds of factors other than the cardiac cycle may also be considered. Examples of the factors include the examination time (i.e., the burden on the patient), the response time of the optical scanner 42 (i.e., scan intervals), and the response time of the optical detector 115 (i.e., scan intervals).

(Cross Sectional Image Forming Unit)

The cross sectional image forming unit 221 forms a cross sectional image (referred to as a first cross sectional image) that represents chronological change in morphology in the first cross section based on detection results of the interference light LC acquired through the first scan. This image formation will be described more in detail. As mentioned above, the first scan is iterative scan of the first cross section C0. During the first scan, detection signals are successively input from the optical detector 115 of the OCT unit 100 to the cross sectional image forming unit 221. Based on detection signals corresponding to each single scan of the first cross section C0, the cross sectional image forming unit 221 forms a single cross sectional image in the first cross section C0. The cross sectional image forming unit 221 iterates such image formation as many times as the number of repetition of the first scan. Thereby, the cross sectional image forming unit 221 forms a series of cross sectional images arranged in time series order. The cross sectional image forming unit 221 may divide these cross sectional images into a plurality of groups and synthesize (e.g., average) cross sectional images in each group to improve image quality.

The cross sectional image forming unit 221 forms a cross sectional image (referred to as a second cross sectional image) that represents morphology in the second cross section C1 based on detection results of the interference light LC acquired through the second scan of the second cross section C1. This image formation is executed in the same manner as for the first cross sectional image. The second cross sectional image may be a single cross sectional image while the first cross sectional image is a series of cross sectional images arranged in time series order. The image quality of the second cross sectional image may be improved by scanning the second cross section C1 a plurality of times and by synthesizing (e.g., averaging) resulting cross sectional images.

Processing of forming such cross sectional images includes noise elimination (noise reduction), filtering, fast Fourier transform (FFT), and the like as in conventional spectral domain OCT techniques. When other type of OCT is applied, the cross sectional image forming unit 221 executes known processing according to the type of OCT.

(Phase Image Forming Unit)

The phase image forming unit 222 forms a phase image that represents chronological change in phase difference in the first cross section based on detection results of the interference light LC acquired through the first scan. The detection results processed here is the same as that processed in the formation of the first cross sectional image performed by the cross sectional image forming unit 221. Accordingly, position matching between the first cross sectional image and the phase image can be performed. That is, pixels in the first cross sectional image and those in the phase image can be associated with each other in a natural manner.

An example of the method of the formation of phase images will be described. A phase image in this example is obtained by calculating the phase differences between adjacent A-line complex signals (that is, signals corresponding to adjacent scan points). In other words, a phase image in this example is formed based on chronological change in the pixel value (brightness value) of each pixel in the first cross sectional image. For any pixel, the phase image forming unit 222 creates a graph of the chronological change in the brightness value of the concerned pixel. The phase image forming unit 222 determines the phase difference $\Delta\varphi$ between two time points t1 and t2 that are apart from each other by a preset time interval $\Delta t$ in the graph. Here, $t2=t1+\Delta t$. The phase difference $\Delta\varphi$ is defined as the phase difference $\Delta\varphi(t1)$ at the time point t1. More generally, the phase difference $\Delta\varphi$ may be defined as the phase difference at any time point between t1 and t2 (including t1 and t2). By executing such processing for each of a plurality of time points set in advance, the chronological change in the phase difference at the concerning pixel.

A phase image is formed by representing, as an image, the values of the phase differences at the respective time points for the respective pixels. Such imaging processing can be realized by representing the values of the phase differences with colors. It is possible to assign different colors to a case where phase increases with the lapse of time and a case where it decreases. For example, red is assigned to the former case while blue is assigned to the latter case. It is also possible to represent the magnitude of the amount of change in phase with the density of display color. With such representation methods, the direction and/or magnitude of blood flow can be clearly represented with colors. The processing described here is applied to each pixel. Thereby, a phase image is formed.

The time interval M is set sufficiently small to secure phase correlation. This allows to obtain the chronological change in phase difference. Here, oversampling is executed in which the time interval Δt is set to be a value smaller than the period corresponding to the resolution of cross sectional images in the scan with the measurement light LS.

(Data Processor)

The data processor 230 executes various kinds of data processing. For example, the data processor 230 applies various kinds of image processing, analysis, or the like to images formed by the image forming unit 220. The data processor 230 can execute various kinds of image correction such as brightness correction or dispersion correction. In addition, the data processor 230 applies various kinds of image processing, analysis, or the like to images (e.g., fundus images, anterior eye images) acquired by the fundus camera unit 2.

The data processor 230 includes the setting processor 231, the blood flow information generation unit 232, and the blood vessel determination unit 233.

(Setting Processor)

The setting processor 231 executes processing for setting a location (referred to as a measurement location) at which blood flow measurement is performed. The processing is executed by analyzing an image of the fundus Ef. The image to be analyzed may be a front image, a cross sectional image or a three-dimensional image of the fundus Ef. In addition, the image to be analyzed may be (a frame of) an observed image, a photographed image, or an OCT image. The setting processor 231 includes the image region specification unit 2311 and the measurement location setting unit 2312.

(Image Region Specification Unit)

The image region specification unit 2311 analyzes the image of the fundus Ef to specify an image region corresponding to a predetermined site of the fundus Ef. Examples of the image region to be specified include an image region corresponding to a blood vessel (referred to as a blood vessel region) and an image region corresponding to the optic nerve head (referred to as an optic nerve head region). In addition, it is also possible to employ a configuration that specifies an image region corresponding to a lesion (referred to as a lesion region) or the like. Analysis for specifying such image regions may be a known technique and may include, for example, processing based on pixel values (e.g., brightness values) (threshold processing, etc.), pattern analysis (e.g., pattern matching), a feature detection process (e.g., edge detection), arbitrary filtering, and the like.

A process of specifying a blood vessel region will be described. The image region specification unit 2311 specifies a plurality of blood vessel regions by analyzing the image of the fundus Ef. The number of the blood vessel regions to be specified may be set in advance or may be an arbitrary number according to the analysis to be executed. Example of the former include a default number or a number set in advance by the user or the like. As an example of the latter, blood vessel regions that meet a predetermined condition can be selected. Examples of the condition include the width of a blood vessel region (referred to as the blood vessel diameter), the location of a blood vessel region, and the like. The location of the blood vessel region may be, for example, the distance from a predetermined site of the fundus Ef (such as the optic nerve head), or the direction with respect to a predetermined site (e.g., the upper side, lower side, ear side, nose side).

The process of calculating the width of the blood vessel region may be an arbitrary process for calculating the width of the belt-shaped or tubular image region. This process includes, for example, the following series of processes: a process of detecting the boundary (or contour) of the blood vessel region (e.g., edge detection); a process of specifying the central axis of the blood vessel region (e.g., thinning); a process of specifying two intersections where a line segment orthogonal to the central axis intersects with the boundary; and a process of calculating the distance between the two intersections.

It is possible to employ a configuration that sets an order of priority to the blood vessel regions based on a predetermined condition and selects a plurality of blood vessel regions from the blood vessel regions according to the order of priority. For example, a configuration may be employed which ranks in descending order of their widths, and selects a predetermined number of blood vessel regions from the upper rank or selects blood vessel regions with widths equal to or larger than a predetermined width value. Alternatively, it is possible to preferentially select a blood vessel region located in a predetermined direction, or to select a blood vessel region so as to be averaged with respect to the direction. When the number of blood vessel regions that satisfy the predetermined condition does not reach a predetermined number, the selection of blood vessel regions may be executed in such a manner that all blood vessel regions that satisfy the predetermined condition are included and some blood vessel regions that does not satisfy the predetermined condition are included.

(Measurement Location Setting Unit)

The measurement location setting unit 2312 sets a plurality of measurement locations that intersects with the plurality of blood vessel regions specified by the image region specification unit 2311. Here, the number of the measurement locations to be set is equal to or less than the number of the plurality of blood vessel regions.

Each of the plurality of measurement locations referred to here may be a concept indicating the first cross section described above. In this case, the measurement location setting unit 2312 performs, in addition to the setting of the plurality of first cross sections, the setting of the second cross sections related to each of the first cross sections. In another example, the plurality of measurement locations referred to here may be a concept indicating both the first cross section and the second cross section. In this case, two or more measurement locations are assigned to each of the blood vessel regions.

The measurement location setting unit 2312 sets, for example, measurement locations (e.g., only the first cross sections, or both the first cross sections and the second cross sections) in an area within a predetermined distance from a predetermined site of the fundus Ef. Here, the predetermined distance is defined as, for example, a distance from an arbitrary characteristic position (e.g., the center position, the center of gravity, the boundary, etc.) of the predetermined site.

Figure 6:
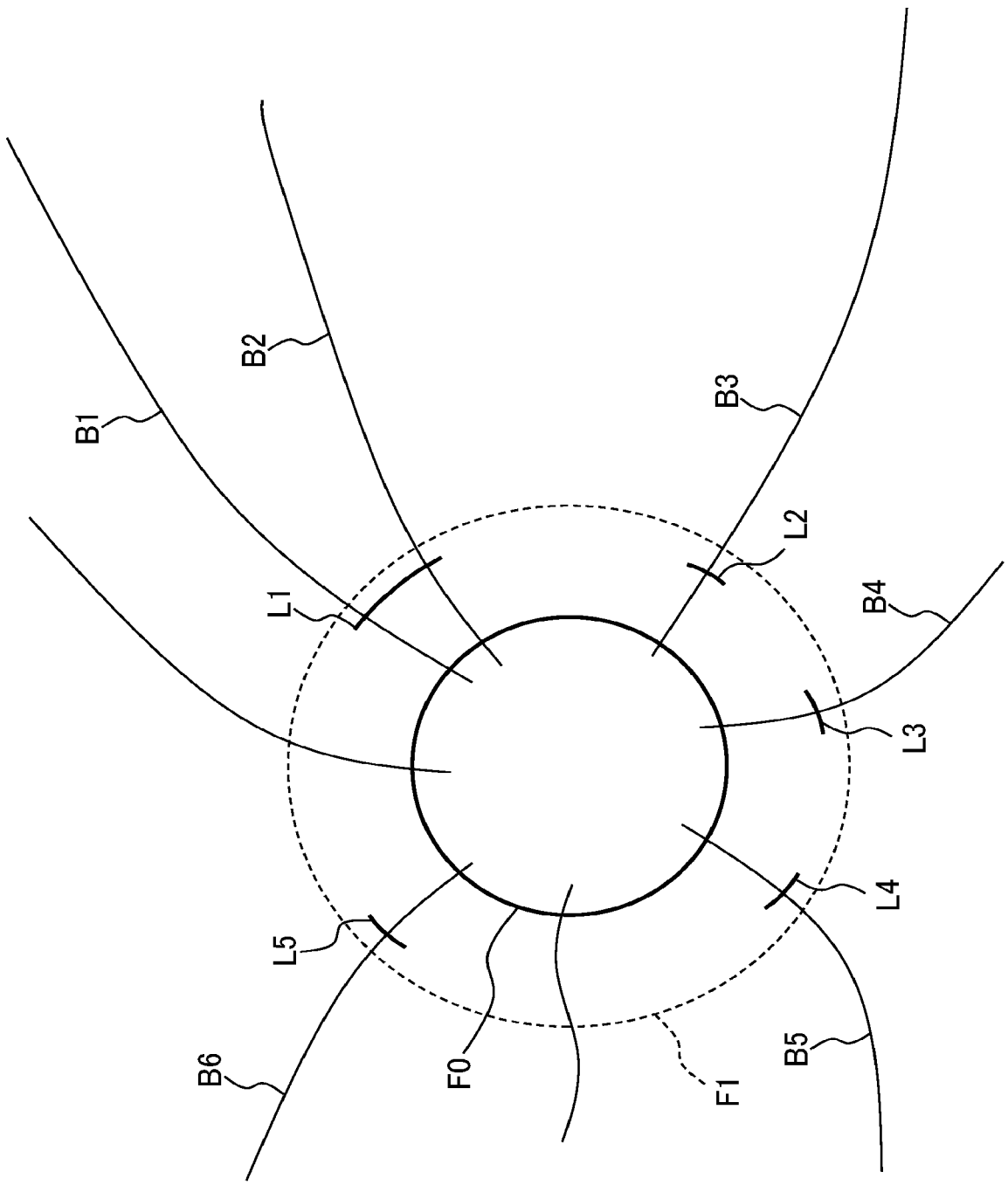
FIG. 6 is a schematic diagram illustrating an example of the operation of the blood flow measurement apparatus according to the embodiment.

FIG. 6 shows an example of the plurality of measurement locations set by the measurement location setting unit 2312. In this example, the predetermined site of the fundus Ef is the optic nerve head. The symbol F0 indicates the optic nerve head region. The symbol F1 indicates an area (referred to as a setting area) within a predetermined distance away from the center of the optic nerve head region F0. The symbols B1 to B6 indicate a plurality of blood vessel regions specified by the image region specification unit 2311.

The measurement location setting unit 2312 sets a plurality of measurement locations in such a manner that they intersect with all the blood vessel regions B1 to B6. In other words, each of the measurement locations is set to intersect with at least one blood vessel region Bi. In this example, the five measurement locations L1 to L5 are set in such a manner that they intersect with the six blood vessel regions B1 to B6. More specifically, the measurement location L1 is set to intersect with the two blood vessel regions B1 and B2, the measurement location L2 is set to intersect with the blood vessel region B3, the measurement location L3 is set to intersect with the blood vessel region B4, the measurement location L4 is set to intersect with the blood vessel region B5, and the measurement location L5 is set to intersect with the blood vessel region B6. It should be noted that measurement locations may be individually set for each blood vessel region, or any measurement location may be set to intersect with two or more blood vessel regions. In addition, each measurement location Lj indicates the first cross section where measurement for obtaining a phase image is performed. The second cross section where the measurement for obtaining the gradient of the blood vessel is performed is set in the vicinity of the first cross section as described above (illustration is omitted).

The shape of the measurement location is arbitrary, and may be, for example, an arc shape as shown in FIG. 6 or a straight line shape. The shapes of the plurality of measurement locations may be the same or different. Also, the length of the measurement location may be arbitrary (for example, a predetermined length). The lengths of the plurality of measurement locations may be the same or different. It is also possible to employ a configuration that sets a maximum value of the length (referred to as a maximum length) of measurement locations in advance and sets a plurality of measurement locations based on the arrangement (e.g., the intervals) of the plurality of blood vessel regions and the maximum length.

Each measurement location Lj (j=1 to 5) is set within the setting area F1. Here, each measurement location Lj (j=1 to 5) can be set on the boundary of the setting area F1. In this case, the measurement location setting unit 2312 can specify the intersecting location between each blood vessel region Bi and the boundary of the setting area F1, and can set the measurement locations so as to pass through the specified plurality of intersecting locations.

For example, each measurement location Lj is set to be orthogonal to the blood vessel region Bi. When one measurement location intersects with two or more blood vessel regions, it is possible to set the one measurement location having a shape that is orthogonal to all the two or more blood vessel regions, or to optimize the placement of the one measurement location with a predetermined shape (that is, it is possible to optimize the position and orientation of the one measurement location).

(Blood Flow Information Generation Unit)

Based on the data acquired by OCT performed according to the plurality of measurement locations set by the measurement location setting unit 2312, the blood flow information generation unit 232 generates information on the blood flow in blood vessels of the fundus Ef (i.e., blood flow information). The blood flow information generation unit 232 includes the blood vessel cross section specification unit 2321, the gradient calculation unit 2322, the blood flow velocity calculation unit 2323, the blood vessel diameter calculation unit 2324, the blood flow amount calculation unit 2325, and the correction unit 2326.

The blood vessel cross section specification unit 2321, the gradient calculation unit 2322, the blood flow velocity calculation unit 2323, the blood vessel diameter calculation unit 2324, and the blood flow amount calculation unit 2325 execute processing to be described later on each measurement location Lj set by the measurement location setting unit 2312. In the following description, the interested blood vessel Db corresponds to each blood vessel region Bi.

(Blood Vessel Cross Section Specification Unit)

The blood vessel cross section specification unit 2321 specifies a blood vessel cross section corresponding to the interested blood vessel Db for each of the first cross sectional image, the second cross sectional image, and the phase image. This specification processing can be executed by analyzing the pixel values of each image. This analysis may include thresholding.

While the first cross sectional image and the second cross sectional image have enough resolution to apply the analysis, the phase image may not have enough resolution to specify the boundary (i.e., contour) of the blood vessel cross section. However, since the phase image is used for the generation of blood flow information, the blood vessel cross section in the phase image must be specified with high precision and high accuracy. On that account, the following processing can be employed to specify the blood vessel cross section in the phase image with higher accuracy.

As described above, the first cross sectional image and the phase image are formed based on the common detection signals, and the pixels of the first cross sectional image and those of the phase image can be associated in a natural manner. Using this association, the blood vessel cross section specification unit 2321 first analyzes the first cross sectional image to determine the blood vessel cross section in the first cross sectional image, and then determines the image region in the phase image consisting of the pixels corresponding to the pixels included in the blood vessel cross section in the first cross sectional image. The image region determined is regarded as the blood vessel cross section in the phase image. With such processing, the blood vessel cross section in the phase image can be specified with high precision and high accuracy.

(Gradient Calculation Unit)

Based on the distance between the first cross section and the second cross section (referred to as cross section interval) and the result of the specification of the blood vessel cross sections, the gradient calculation unit 2322 calculates the gradient (or, inclination or tilt) of the interested blood vessel Db at the first cross section. The cross section interval is set in advance to be the distance between the first cross section and the second cross section set by the measurement location setting unit 2312.

The gradient of the interested blood vessel Db is calculated for the following reason. The blood flow information is obtained by using Doppler OCT technique. The velocity component of blood flow contributing to Doppler shift is the component in the projection direction of the measurement light LS. Therefore, even when the blood flow velocity is the same, Doppler shift given to the measurement light LS changes according to the angle between the blood flow direction (i.e., the gradient of the interested blood vessel) and the projection direction of the measurement light LS. Thereby, the blood flow information acquired is also changed. In order to avoid such a problem, it is necessary to determine the gradient of the interested blood vessel Db and perform the calculation of the blood flow velocity based on the gradient.

Figure 7:
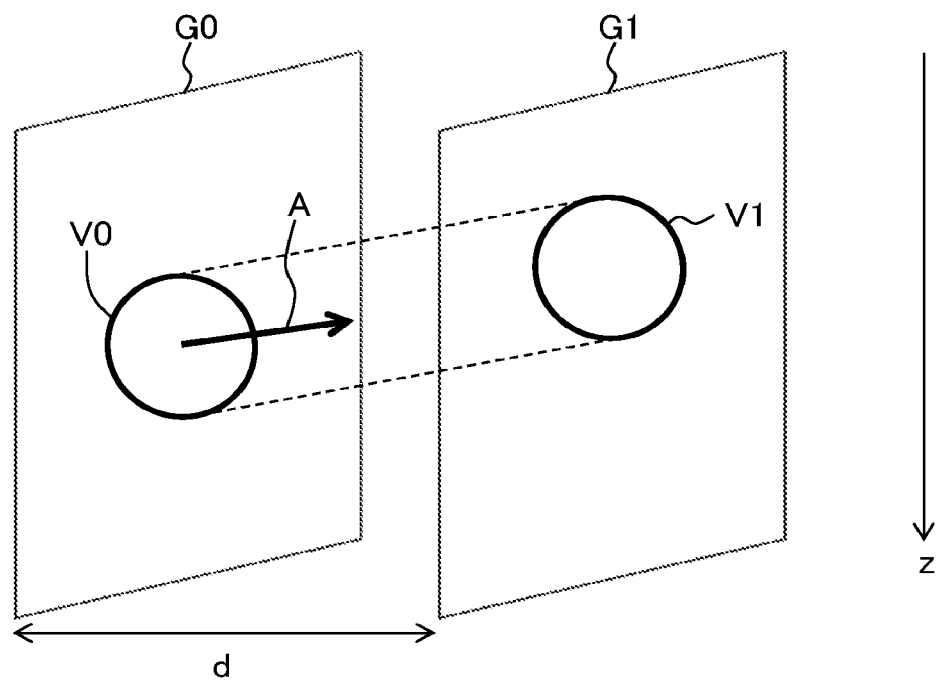
FIG. 7 is a schematic diagram illustrating an example of the operation of the blood flow measurement apparatus according to the embodiment.
Figure 8:
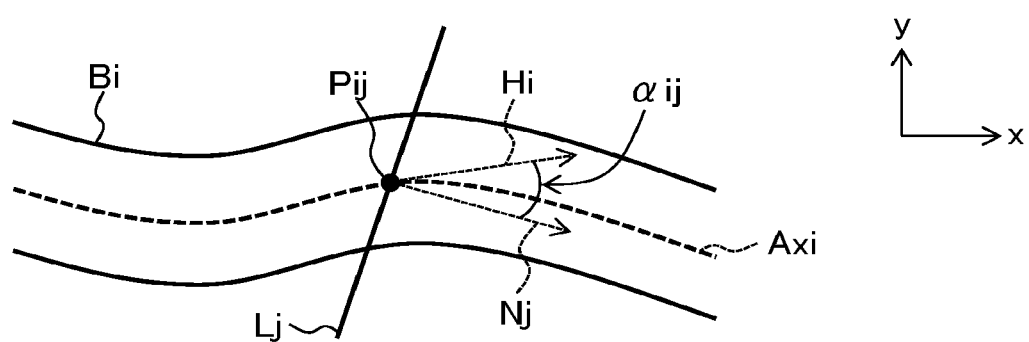
FIG. 8 is a schematic diagram illustrating an example of the operation of the blood flow measurement apparatus according to the embodiment.

A method of calculating the gradient of the interested blood vessel Db will be described with referring to FIG. 7. The symbol G0 indicates the first cross sectional image of the first cross section C0, and the symbol G1 indicates the second cross sectional image of the second cross section C1. The symbol V0 indicates the blood vessel cross section in the first cross sectional image G0, and the symbol V1 indicates the blood vessel cross section in the second cross sectional image G1. In FIG. 7, the z coordinate axis is oriented downward, and substantially coincides with the projection direction of the measurement light LS. Further, the cross section interval is indicated by "d".

The gradient calculation unit 2322 calculates the gradient "A" of the interested blood vessel Db at the first cross section C0 based on the positional relationship between the two blood vessel cross sections V0 and V1. The positional relationship is obtained, for example, by connecting the two blood vessel cross sections V0 and V1. More specifically, the gradient calculation unit 2322 specifies a representative point in the blood vessel cross section V0 and a representative point in the blood vessel cross section V1, and connects the two representative points with a line segment. The representative point may be the center position, the position of the center of gravity, the highest position (the position corresponding to the smallest z coordinate value), the lowest position (the position corresponding to the largest z coordinate value), or the like.

Further, the gradient calculation unit 2322 calculates the gradient A based on the line segment connecting the two representative points. More specifically, the gradient calculation unit 2322 calculates the gradient of the line segment connecting the representative point in the first cross section C0 and the representative point in the second cross section C1, and set the calculated value to be the gradient A. The cross section interval "d" is used, in the calculation of the line segment, to embed the two cross sectional images G0 and G1 in the xyz coordinate system.

In the present example, a single value is obtained for the gradient. However, two or more gradients corresponding to two or more positions in the blood flow cross section V0 may be obtained. In such a case, the obtained two or more gradient values may be used separately. Alternatively, it is possible to execute statistical calculation to obtain a single value (e.g., mean value) from the obtained two or more gradient values, and set the obtained single value to be the gradient A.

(Blood Flow Velocity Calculation Unit)

Based on the phase image (i.e., chronological change in phase difference) and the gradient A of the interested blood vessel Db, the blood flow velocity calculation unit 2323 calculates the blood flow velocity at the first cross section C0 for the blood flowing through the interested blood vessel Db.

The parameter to be calculated may be the blood flow velocity at a certain time point, or may be the chronological change in the blood flow velocity. The chronological change in the blood flow velocity is referred to as blood flow velocity variation information. When the blood flow velocity at a certain time point is determined, the blood flow velocity at a predetermined time phase in an electro cardiogram (e.g., time phase corresponding to R wave) may be selectively acquired. When the blood flow velocity variation information is determined, the range of the measurement period is the whole or an arbitrary part of the period taken for the scan of the first cross section C0.

When the blood flow velocity variation information is acquired, the blood flow velocity calculation unit 2323 can further calculate a statistic of the blood flow velocity in the measurement period. Examples of the statistic include the mean value, the standard deviation, the variance, the median, the global maximum, the global minimum, the local maximum, and the local minimum. The blood flow velocity calculation unit 234 can also create a histogram on the blood flow velocity values.

The blood flow velocity calculation unit 2323 calculates the blood flow velocity using Doppler OCT technique as described above. In the blood flow velocity calculation, the gradient A of the interested blood vessel Db at the first cross section C0 calculated by the gradient calculation unit 2322 is taken into account. Specifically, the blood flow velocity calculation unit 2323 applies the following formula to the blood flow velocity calculation.

$$\Delta f = \frac{2nv\cos\theta}{\lambda} \quad \text{(Formula 1)}$$

Here:
$\Delta f$ indicates the Doppler shift given to scattered light of the measurement light LS;
n indicates the refractive index of medium;
v indicates the flow velocity of the medium (blood flow velocity);
$\theta$ indicates the angle between projection direction of the measurement light LS and the flow vector of the medium; and
$\lambda$ indicates the center wavelength of the measurement light LS.

In the present embodiment, n and $\lambda$ are known, $\Delta f$ is obtained from the chronological change of the phase difference, and $\theta$ is obtained from the gradient A (alternatively, $\theta$ is obtained as the gradient A). The blood flow velocity v is calculated by substituting these values into the above formula.

When the chronological changes in the parameters are taken into account, it can be expressed that the Doppler shift $\Delta f = \Delta f(t)$ and the angle $\theta = \theta(t)$. Here, t is a variable representing time. The blood flow velocity calculation unit 2323 can use the following formula to determine the blood flow velocity v(t) at an arbitrary time, or to determine the chronological changes in the blood flow velocity v(t).

$$\Delta f(t) = \frac{2nv(t)\cos\theta(t)}{\lambda} \quad \text{(Formula 2)}$$

(Blood Vessel Diameter Calculation Unit)

The blood vessel diameter calculation unit 2324 calculates the diameter of the interested blood vessel Db at the first cross section C0. Examples of this calculation include the first calculation method that utilizes a fundus image and the second calculation method that utilizes a cross sectional image.

When applying the first calculation method, an area of the fundus Ef including the location of the first cross section C0 is photographed in advance. The fundus image thus obtained may be an observation image (e.g., a frame(s) thereof), or may be a photographed image. When the photographed image is a color image, any image obtained from the color image (e.g., a red-free image) may be used.

The blood vessel diameter calculation unit 2324 sets a scale of the fundus image based on various kinds of factors that determines the relationship between the scale of images and the scale in the real space such as the photographing angle of view (photographing magnification), the working distance, information on eyeball optical system. The scale of the fundus image may represent length in the real space. As a specific example, the scale associates interval between adjacent pixels with the scale in the real space (e.g., pixel interval=10 μm). It is possible to determine, in advance, the relationship between various values of the above factors and the scale in the real space, and store a table or a graph that represents the determined relationship. In this case, the blood vessel diameter calculation unit 2324 selects the scale corresponding to the above factors, and uses the selected scale.

Based on the scale and the pixels included in the blood vessel cross section V0, the blood vessel diameter calculation unit 2324 calculates the diameter of the interested blood vessel Db at the first cross section C0, that is, the diameter of the blood vessel cross section V0. As a specific example, the blood vessel diameter calculation unit 2324 may calculate the maximum or the mean value of a plurality of diameters of the blood vessel cross section V0 corresponding to different directions. The blood vessel diameter calculation unit 2324 may determine an approximate circle or an approximate ellipse of the contour of the blood vessel cross section V0, and calculate the diameter of the approximate circle or the approximate ellipse. Note that once the blood vessel diameter of the blood vessel cross section V0 is determined, the area of the blood vessel cross section V0 can (substantially) be calculated. That is, it is possible to substantially associate the blood vessel diameter with the area in one-to-one fashion. Hence, the area can be calculated in place of the blood vessel diameter.

The second calculation method will be described. In the second calculation method, a cross sectional image of the fundus Ef at the first cross section C0 is used. The cross sectional image may be the first cross sectional image, the phase image, or any other image.

The scale of the cross sectional image is determined according to the scan mode of the measurement light LS. In the present embodiment, the first cross section C0 is scanned as shown in FIG. 5. The length of the first cross section C0 is determined based on various kinds of factors that define the relationship between the scale of an image and the scale in the real space such as the working distance, the information about eyeball optical system. The blood vessel diameter calculation unit 2324, for example, determines the interval between adjacent pixels based on the length of the first cross section C0, and calculates the diameter of the interested blood vessel Db at the first cross section C0 in the same manner as in the first calculation method. The chronological change in the blood vessel diameter can also be determined.

(Blood Flow Amount Calculation Unit)

Based on the calculation result of the blood flow velocity and the calculation result of the blood vessel diameter, the blood flow amount calculation unit 2325 calculates the flow amount (or, flow volume or flow rate) of the blood that flows through the interested blood vessel Db. An example of this processing will be described below.

It is assumed that the blood flow in a blood vessel is the Hagen-Poiseuille flow. The blood vessel diameter is denoted by w, and the maximum blood flow velocity is denoted by Vm. Then, the blood flow amount Q is expressed as in the following formula.

$$Q = \frac{\pi w^2}{8} Vm \qquad \text{(Formula 3)}$$

The blood flow amount calculation unit 2325 substitutes the blood vessel diameter w calculated by the blood vessel diameter calculation unit 2324 and the maximum blood flow velocity Vm based on the blood flow velocity calculated by the blood flow velocity calculation unit 2323 into this formula to determine the blood flow amount Q. In another example, the blood flow amount calculation unit 2325 executes the time integration of the product (or the integrated value) of the chronological change of the blood flow velocity and the blood vessel diameter (or the chronological change thereof) to determine the blood flow amount Q. The unit of the blood flow amount Q is, for example, μL/min.

By the processing described above, the blood vessel diameter, the blood flow velocity, and the blood flow amount can be obtained for each blood vessel region Bi. The blood flow amount calculation unit 2325 can determine the total blood flow amount based on the plurality of blood flow amounts calculated for the plurality of blood vessel regions B1 to B6. The total blood flow amount may be a simple sum of the plurality of blood flow amounts calculated or a weighted sum thereof. Alternatively, considering that the sum of the plurality of blood flow amounts is less than the sum total of the blood flow amounts of all blood vessels of the fundus Ef, the total blood flow amount may be determined by adding or multiplying a predetermined factor to the sum of the plurality of blood flow amounts. This factor is calculated, for example, based on any of the following values: a ratio (or a difference) calculated based on the number of all blood vessels that can be specified from the fundus image or the OCT image and the number of blood vessels considered for calculating the blood flow amount; blood vessel diameters; data on blood vessels, blood flow amount, or the like clinically (statistically) obtained; and examination data obtained in the past about the subject's eye concerned (or the subject concerned).

(Correction Unit)

The correction unit 2326 corrects the calculated blood flow information (e.g., the blood flow velocity, the blood vessel diameter, the blood flow rate). This correction processing is executed, for example, based on the angle formed by the interested blood vessel (i.e., the blood vessel region Bi) and the cross section intersecting with the interested blood vessel (i.e., the measurement location Lj). The correction unit 2326 calculates this angle. Alternatively, when a configuration that calculates the angle in the processing of the preceding stage is employed, the calculated angle is input to the correction unit 2326.

The processing of calculating the angle includes, for example, the following series of processes: a process of determining the central axis Axi of the blood vessel region Bi by applying image processing such as thinning of the blood vessel region Bi; a process of determining the intersection Pij of the central axis Axi and the measurement location Lj; a process of determining the tangential direction Hi of the central axis Axi at the intersection Pij (here, an approximate curve of the central axis Axi can be determined as necessary); a process of determining the normal direction Nj of the measurement location Lj at the intersection Pij (alternatively, a process of determining the direction orthogonal to the tangential direction of the measurement location Lj at the intersection Pij); and a process of determining the angle $\alpha ij$ formed by the tangential direction Hi and the normal direction Nj.

As described above, it is desirable to set the measurement location Lj to be orthogonal to the direction of the course of the blood vessel region Bi. In other words, it is desirable to set the measurement location Lj so that the normal direction Nj coincides with the tangential direction Hi of the blood vessel region Bi (therefore, the smaller value of the angle $\alpha ij$ is preferable). In this manner, it can be said that the angle $\alpha ij$ is a parameter that indicates the suitability of the set measurement location Lj.

The correction unit 2326 can determine the suitability of the measurement location Lj based on the calculated angle $\alpha ij$. For example, the correction unit 2326 compares the calculated angle $\alpha ij$ with a predetermined threshold value. When the angle $\alpha ij$ is smaller than the threshold value, the correction unit 2326 does not correct the blood flow information for the blood vessel region Bi. On the other hand, when the angle $\alpha ij$ is equal to or larger than the threshold value, the correction unit 2326 corrects the blood flow information acquired for the blood vessel region Bi concerned. Such correction processing includes, for example, a process of converting the value of blood flow information by applying trigonometry using the angle $\alpha ij$.

The use of the angle $\alpha ij$ is not limited to the correction of blood flow information. For example, it is possible to employ a configuration that sets the measurement location Lj again when the angle $\alpha ij$ is equal to or larger than the threshold value. In another example, it is possible to provide, to the user, the angle $\alpha ij$ or a value calculated from the angle $\alpha ij$ as an evaluation value that indicates the reliability of the blood flow information.

(Blood Vessel Determination Unit)

The blood vessel determination unit 233 determines whether the blood vessel region Bi is an image region corresponding to an artery (referred to as an artery region) or an image region corresponding to a vein (referred to as a vein region). This determination processing is executed, for example, on the basis of the pixel values of the fundus image (see Japanese Unexamined Patent Application Publication No. 2007-319403, etc.). Alternatively, the determination of the blood vessel region may be performed based on the distribution of blood vessels in the fundus Ef and the phase image. Specifically, the blood vessel determination unit 233 determines a route of the blood vessel region Bi from the optic nerve head to the measurement location Lj based on the blood vessel distribution represented in a fundus image, determines the blood flow direction of the blood vessel region Bi at the measurement location Lj based on the phase image, and determines whether the blood vessel region Bi is an artery region or a vein region based on the route and blood flow direction determined.

On the basis of the determination result obtained by the blood vessel determination unit 233, the blood flow amount calculation unit 2325 can separately determine the total blood flow amount for artery regions and the total blood flow amount for vein regions.

The data processor 230 having the above functions includes, for example, a microprocessor, RAM, ROM, hard disk drive, circuit board, and the like. Computer programs for the microprocessor to execute the above functions are stored, in advance, in the storage device such as the hard disk drive.

(User Interface)

A user interface 240 includes the display unit 241 and the operation unit 242. The display unit 241 includes the aforementioned display device of the arithmetic and control unit 200, the display device 3, and the like. The operation unit 242 includes the aforementioned operation devices of the arithmetic and control unit 200. The operation unit 242 may also include various kinds of buttons, keys, etc. that are arranged on the housing of the blood flow measurement apparatus 1 or are peripheral equipment. For example, when the housing of the fundus camera unit 2 is similar to that of the conventional fundus camera, the operation unit 242 may include a joy stick, an operation panel, etc. arranged on the housing. The display unit 241 may include various kinds of display devices such as a touch panel monitor arranged on the housing of the fundus camera unit 2.

The display unit 241 and the operation unit 242 do not need to be individual devices. For example, like a touch panel, a device having both the display function and the operation function can be employed. In such a case, the operation unit 242 includes a touch panel and computer programs. Contents of operation performed using the operation unit 242 are input into the controller 210 as electrical signals. Further, operation and information input may be carried out using the GUI displayed on the display unit 241 and the operation unit 242.

<Operation>

Several examples of the operation of the blood flow measurement apparatus 1 will be described.

(First Operation Example)

Figure 9:
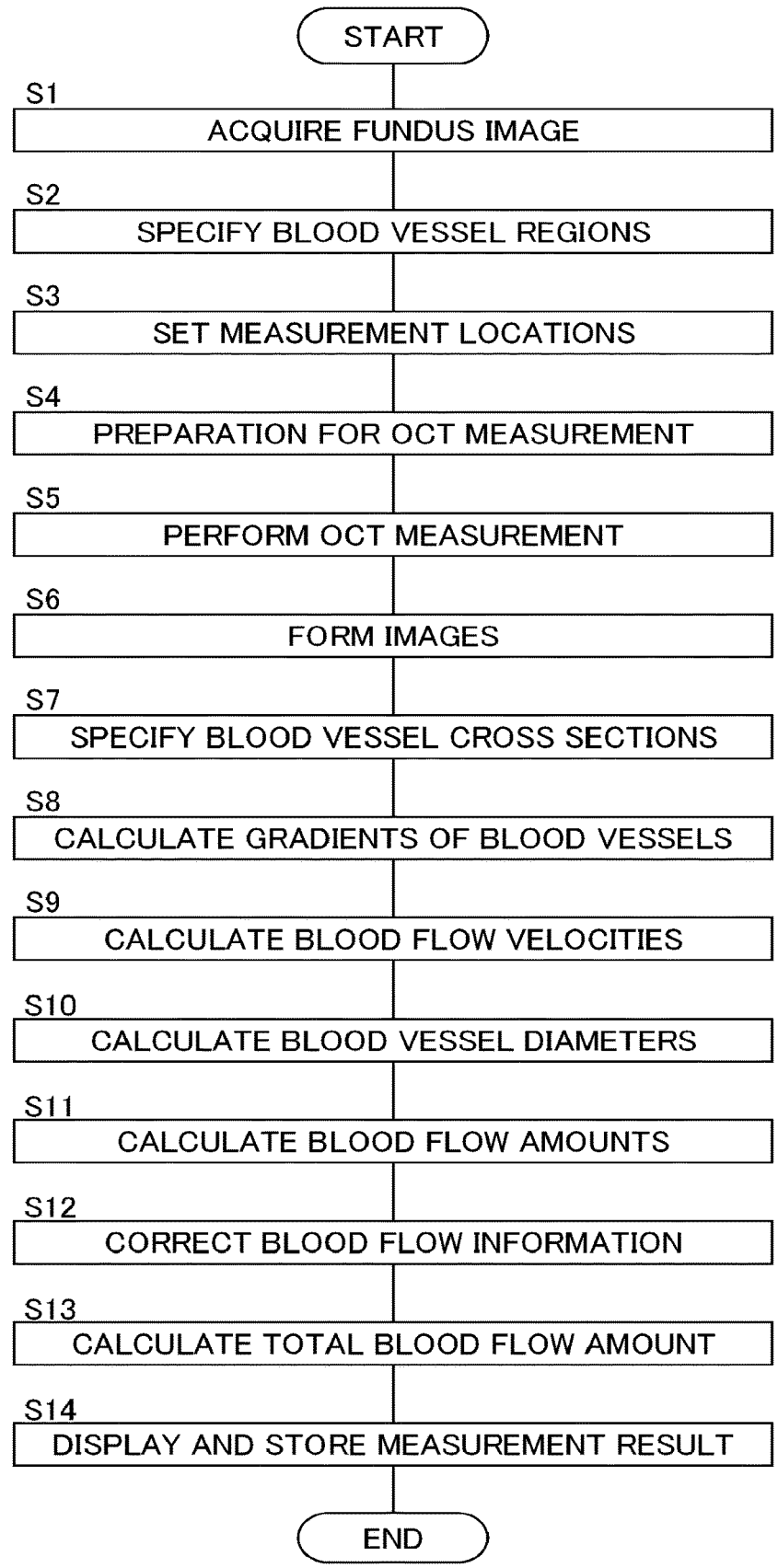
FIG. 9 is a flowchart illustrating an example of the operation of the blood flow measurement apparatus according to the embodiment.

An example of the operation of the blood flow measurement apparatus 1 is shown in FIG. 9. A preliminary procedure such as input of patient ID and selection of an operation mode (i.e., blood flow measurement mode) is performed in advance.

(S1: Acquire Fundus Image)

First, the blood flow measurement apparatus 1 acquires an image of the fundus Ef for setting the measurement location (referred to as a setting image). The setting image is an image obtained by photographing the fundus Ef using the blood flow measurement apparatus 1 or another fundus imaging apparatus, and is, for example, an observation image, a photographed image or an OCT image of the fundus Ef. When the setting image is acquired by another fundus imaging apparatus, the blood flow measurement apparatus 1 obtains the setting image from the fundus imaging apparatus, an image archiving server, or the like. The setting image may be an image acquired in real time by the blood flow measurement apparatus 1 (for example, an observation image or an OCT image), or an image acquired in the past by the blood flow measurement apparatus 1 or another fundus imaging apparatus (for example, an observation image, a photographed image, or an OCT image).

(S2: Specify Blood Vessel Regions)

The image region specification unit 2311 analyzes the setting image acquired in step S1, thereby specifying a plurality of blood vessel regions Bi. It is also possible to further specify the nerve head region or the like at this stage.

(S3: Set Measurement Locations)

Next, the measurement location setting unit 2312 sets a plurality of measurement locations Lj (i.e., first cross sections) that intersects with the plurality of blood vessel regions Bi specified in step S2. In addition, the measurement location setting unit 2312 sets a second cross section in the vicinity of each measurement location Lj.

The main controller 211 can control the display unit 241 to display the setting image and the information indicating the plurality of measurement locations Lj (and the second cross sections). The user can adjust any of the measurement locations Lj, delete any of the measurement locations Lj, or add a new measurement location.

(S4: Preparation for OCT Measurement)

Next, preparation for OCT measurement (i.e., blood flow measurement) is executed. This processing includes, for example, alignment and focus adjustment. Furthermore, tracking can be started. When the OCT measurement is performed in step S1, such processing is executed in step S1.

Further, processing for specifying the scanning locations in the fundus Ef corresponding to the measurement location Lj (i.e., the first cross sections) and the second cross sections set for the setting image can be executed. This processing includes, for example, a process of acquiring an observation image of the fundus Ef in real time, an image matching between the observation image (frames thereof) and the setting image, and a process of specifying locations (i.e., scanning locations) in the observation image corresponding to the measurement locations Lj (i.e., the first cross sections) and the second cross sections based on the image matching. For the plurality of scanning locations specified in this way, the OCT measurement in step S5 is executed.

At this stage, OCT measurement conditions can be optimized. In the optimization processing, for example, the main controller 211 controls the light source unit 101, the optical scanner 42, etc. to perform preparatory OCT measurement. The preparatory OCT measurement is applied to any of the measurement locations set in step S3 (e.g., any of the first cross sections, any of the second cross sections), or to another cross section. Then, it is determined whether an image acquired through the preparatory OCT measurement is adequate or not. The determination may be carried out through the visual observation by the user. Alternatively, the determination may be automatically executed by the blood flow measurement apparatus 1.

When determining through the visual observation, the main controller 211 displays the OCT image on the display unit 241. The user checks the image quality of the OCT image, the displayed location of a predetermined tissue (e.g., blood vessels, the surface of the retina) in the OCT image, or the like. When the OCT image is inadequate, the user adjusts measurement conditions. For example, when the displayed location is inadequate, the user operates the optical path length changer 41 to adjust the optical path length of the measurement light LS. When the image quality is inadequate, the user operates the optical attenuator 105, the polarization controller 106, or the like.

When the determination is automatically executed, the blood flow measurement apparatus 1 evaluates the image quality, the displayed location of the predetermined tissue, etc. with referring to a predetermined evaluation criterion, and adjusts the measurement conditions based on the result of the evaluation in the same manner as in the manual adjustment.

(S5: Perform OCT Measurement)

Upon completion of the optimization processing in step S4, the main controller 211 executes OCT measurement (i.e., blood flow measurement). In this operation example, an iterative scan (i.e., first scan) of the plurality of measurement locations Lj (i.e., first cross sections) and a scan (i.e., second scan) of the plurality of second cross sections are performed. This process includes a plurality of first scans and a plurality of second scans. The execution order of the first scans and the second scans is set in advance.

(S6: Form Images)

The image forming unit 220 forms a plurality of images based on the data acquired in step S5. In the present operation example, the cross sectional image forming unit 221 forms a first cross sectional image T1$i$ for each of the measurement locations Li (i.e., first cross sections) and a second cross sectional image T2$i$ for each of the second cross sections. Further, the phase image forming unit 222 forms a phase image Ui for each of the measurement locations Li (i.e., first cross sections).

(S7: Specify Blood Vessel Cross Sections)

The blood vessel cross section specification unit 2321 specifies a blood vessel cross section corresponding to the blood vessel region Bi for each of the first cross sectional images T1$i$, each of the second cross sectional images T2$i$, and each of the phase images Ui formed in step S6.

(S8: Calculate Gradients of Blood Vessels)

The gradient calculation unit 2322 calculates, for each blood vessel region Bi, the gradient of the blood vessel region Bi (i.e., the interested blood vessel) at the first cross section based on the blood vessel cross sections specified in step S7 and the distance between the measurement location Lj (i.e., the first cross section) and the second cross section (i.e., cross section interval).

(S9: Calculate Blood Flow Velocities)

For each blood vessel region Bi (i.e., interested blood vessel), based on the chronological change in the phase difference obtained as the phase images Ui and the gradient of the blood vessel region Bi calculated in step S8, the blood flow velocity calculation unit 2323 calculates the blood flow velocity at the measurement location Lj (i.e., first cross section) for the blood flowing through the concerned interested blood vessel.

(S10: Calculate Blood Vessel Diameters)

For each blood vessel region Bi (i.e., interested blood vessel), based on the first cross sectional image T1$i$ (or the phase image Ui), the blood vessel diameter calculation unit 2324 calculates the diameter of the interested blood vessel at the measurement location Lj (i.e., first cross section). Note that the blood vessel diameter may be calculated by analyzing a fundus image instead of the first cross sectional image.

(S11: Calculate Blood Flow Amounts)

For each blood vessel region Bi (i.e., interested blood vessel), based on the blood flow velocity determined in step S9 and the blood vessel diameter determined in step S10, the blood flow amount calculation unit 2325 calculates the flow amount (μL/min) of the blood that flows through the interested blood vessel.

(S12: Correct Blood Flow Information)

The correction unit 2326 calculates an angle α$ij$ formed by each blood vessel region Bi (i.e., interested blood vessel) and the measurement location Lj (i.e., first cross section) intersecting with the concerned blood vessel region Bi. In addition, Based on the calculated angle α$ij$, the correction unit 2326 corrects the blood flow information (e.g., the blood flow velocity, the blood vessel diameter and/or the blood flow amount) for the blood vessel region $B_i$ concerned.

(S13: Calculate Total Blood Flow Amount)

The blood flow amount calculation unit 2325 calculates the total blood flow amount based on the plurality of the blood flow amounts calculated in step S11 (or based on the blood flow amounts corrected in step S12).

At this stage, the blood vessel regions Bi may be classified into artery regions and vein regions by the blood vessel determination unit 233, and the total blood flow amount for the artery regions and the total blood flow amount for the vein regions may be determined.

(S14: Display and Store Measurement Result)

The main controller 211 displays, on the display unit 241, the blood flow information including the blood flow velocities, the blood vessel diameters, the blood flow amounts, etc. obtained for the plurality of blood vessel regions Bi and the total blood flow amount calculated in step S13, and the like. The blood flow information may include information indicating a plurality of measurement locations Lj (referred to as location information), the setting image, etc. In addition, the main controller 211 associates the blood flow information with the patient ID input in advance, and stores it in the storage unit 212. This terminates the processing of the present operation example.

(Second Operation Example)

A process of presenting the plurality of blood vessel regions Bi using a cross sectional image acquired by OCT will be described.

Figure 10:
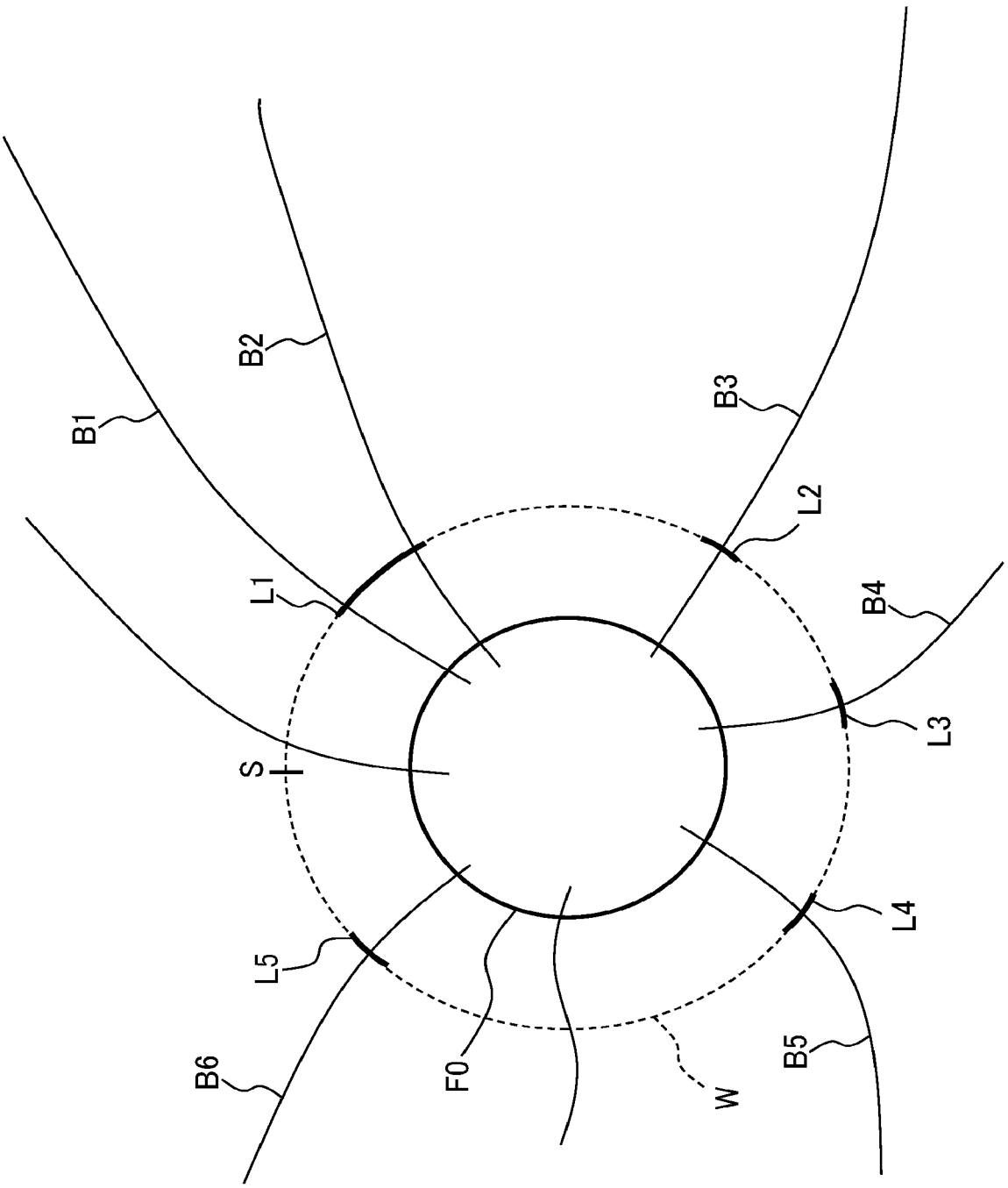
FIG. 10 is a schematic diagram illustrating an example of the operation of the blood flow measurement apparatus according to the embodiment.

In this operation example, for instance, in the OCT measurement in step S5 of the first operation example, scanning of a single cross section including a plurality of measurement locations $L_i$ is additionally carried out. An example of the single cross section is shown in FIG. 10. The scan pattern shown in FIG. 10 is a circle scan that passes through the plurality of measurement locations L1 to L5 and surrounds the optic nerve head region F0.

By executing such a circle scan, a cross sectional image representing the morphology in all the measurement locations Lj (the first cross section) is obtained. In this cross sectional image, a cross section of each blood vessel region Bi is rendered. The main controller 211 can control the display unit 241 to display the cross sectional image, and to display information indicating the cross section of each blood vessel region Bi (referred to as blood vessel location information) on the cross sectional image.

Figure 11:
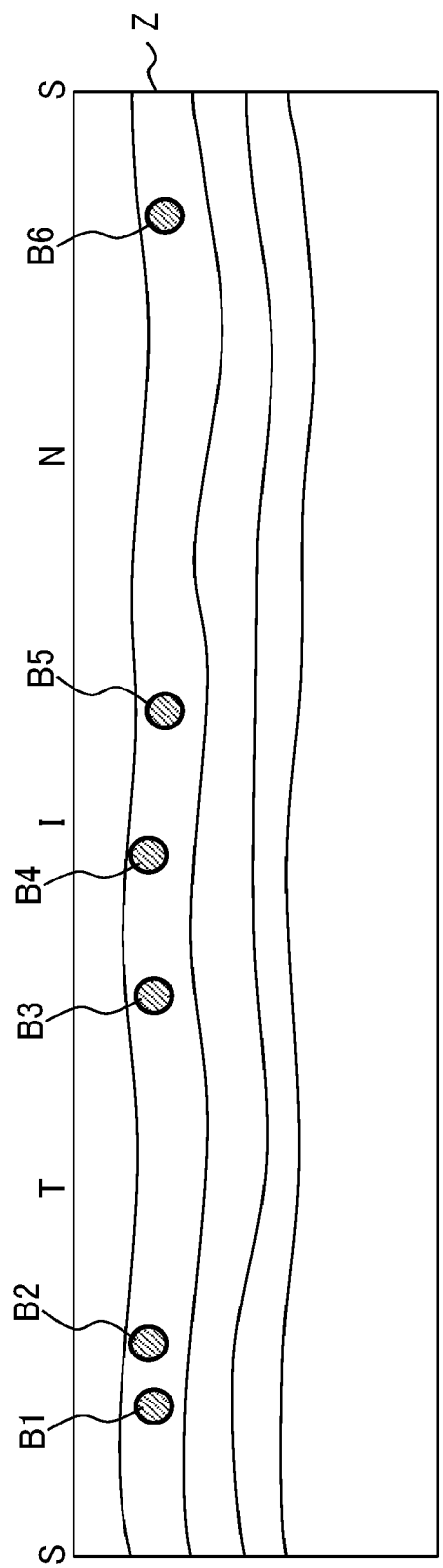
FIG. 11 is a schematic diagram illustrating an example of the operation of the blood flow measurement apparatus according to the embodiment.

An example of the information displayed in this way is shown in FIG. 11. The symbol Z indicates the cross sectional image based on the data acquired by the circle scan of FIG. 10. The cross sectional image Z represents a belt-shaped cross section obtained by cutting and opening a cylindrical scan section corresponding to the circle scan. The cutting location of the cylindrical scan section may be arbitrary. The cross sectional image Z shown in FIG. 11 is obtained by cutting and opening the cylindrical scan section at the location "S" that is at 12 o'clock position in FIG. 10. As is commonly used, "S" represents the upper side (superior), "T" represents the ear side (temporal), "I" represents the lower side (inferior), and "N" represents the nose side (nasal). In addition, on the cross sectional image Z, the blood vessel location information (indicated by the symbols B1 to B6) that indicates (the cross sections of) the blood vessel regions B1 to B6 is displayed.

The user can designate desired blood vessel location information Bi by using the operation unit 242. The main controller 211 can control the display unit 241 to display the blood flow information corresponding to the designated blood vessel location information Bi (i.e. blood vessel region Bi).

It should be noted that a configuration can be employed so that similar processing can be performed on the front image of the fundus Ef. The front image may be, for example, a setting image or a separately acquired image. The main controller 211 displays the front image and also displays the blood vessel location information on the front image. When the user designates desired blood vessel location information, the main controller can control the display unit 241 to display the blood flow information corresponding to the designated blood vessel location information.

<Effects>

Effects of the blood flow measurement apparatus of the embodiment will be described.

The blood flow measurement apparatus of the embodiment includes an image acquisition unit, an image region specification unit, a measurement location setting unit, a scanner and a blood flow information generation unit.

The image acquisition unit includes, for example, a function of imaging a living body. In the present embodiment, the configuration for acquiring the observation images, the photographed images, and/or the OCT images of the eye fundus corresponds to the image acquisition unit. In another example, the image acquisition unit includes a function of acquiring an image from an external device (e.g., another fundus imaging apparatus, an image archiving server, etc.). This function is realized by a configuration including a communication interface. The image region specification unit (2311) is configured to analyze the image acquired by the image acquisition unit to specify a plurality of blood vessel regions. The measurement location setting unit (2312) is configured to set a plurality of measurement locations that intersects with the plurality of blood vessel regions specified by the image region specification unit. The scanner is configured to scan a plurality of cross sections of the living body corresponding to the plurality of measurement locations set by the measurement location setting unit by applying OCT measurement. In the present embodiment, the configuration for acquiring the OCT images of the fundus corresponds to the scanner. The blood flow information generation unit (232) is configured to generate blood flow information on the living body based on the data acquired by the scanner. The blood flow information includes, for example, a blood flow amount, a blood flow velocity, a blood vessel diameter, etc. for each of the blood vessel regions specified by the image region specification unit.

According to the blood flow measurement apparatus thus configured, blood flow measurement of a plurality of blood vessels can be divided into and performed in a plurality of stages (that is, a plurality of measurement locations), so that both a dense scan point intervals and a high iteration rate can be achieved. Therefore, blood flow measurement can be suitably performed even when a plurality of blood vessels distributed over a wide area are targeted.

In the embodiment, the image region specification unit may be configured to calculate the width of a blood vessel region in the image acquired by the image acquisition unit and specify the plurality of blood vessel regions so as to include blood vessel regions for which the calculated widths are equal to or larger than a predetermined threshold value. According to such a configuration, major blood vessels can be automatically selected to perform blood flow measurement.

In the embodiment, the image region specification unit may be configured to analyze the image acquired by the image acquisition unit to specify an image region corresponding to a predetermined site of the living body. An example of the image region is the optic nerve head of the fundus. In addition, the measurement location setting unit may be configured to set the plurality of measurement locations in an area within a predetermined distance away from the image region specified by the image region specification unit. According to such a configuration, blood flow measurement can be performed within an area determined in advance. The area may be arbitrarily set in medical practice or research. In addition, it is possible to configure so that the area can be arbitrarily changed.

In the embodiment, the measurement location setting unit may be configured to set the plurality of measurement locations in such a way that the plurality of measurement locations is orthogonal to at least part of the plurality of blood vessel regions. According to such a configuration, suitable blood flow measurement can be easily performed.

In the embodiment, the scanner may be configured to scan a single cross section that includes the plurality of cross sections. Further, the blood flow measurement apparatus may include a cross sectional image forming unit and a controller. The cross sectional image forming unit (221) is configured to form a cross sectional image representing morphology in the single cross section based on the data acquired by scanning the single cross section. The controller (210) is configured to control a display device to display the cross sectional image and blood vessel location information indicating the locations of a plurality of blood vessels at which the blood flow information is generated. Note that the display device may be provided in the blood flow measurement apparatus (e.g., display unit 241) or may be an external device. According to such a configuration, it is possible to clearly indicate the blood vessels to which the blood flow measurement has been applied as well as the image representing the cross sectional morphology of the living body.

In the embodiment, the blood flow information generation unit may include a correction unit (2326). The correction unit is configured to determine the angle formed by a blood vessel region and a measurement location that intersects with the same blood vessel region, and corrects the blood flow information based on the determined angle. According to such a configuration, it is possible to improve the reliability of the blood flow information to be acquired.

In the embodiment, the blood flow information generation unit may be configured to determine a total blood flow amount based on a plurality of flow amounts determined for the plurality of cross sections. In addition, the blood flow measurement apparatus of the embodiment may include a determination unit (e.g., blood vessel determination unit 233) configured to determine whether a blood vessel region is an artery region or a vein region. Furthermore, the blood flow information generation unit may be configured to determine a total blood flow amount for the artery region and a total blood flow amount for the vein region.

<Modification Examples>

The configurations described above are merely examples for implementing the present invention. Therefore, it is possible to make arbitrary modification (omission, replacement, addition, etc.) within the scope of the present invention.

A modification example of method of calculating blood flow amount will be described. In the present modification example, the blood flow velocity calculation unit 2323 generates information (blood flow velocity variation information) that represents chronological change in the blood flow velocity for each pixel included in the blood vessel region in the phase image. The generation of the blood flow velocity variation information may include: a position matching between a plurality of phase images arranged in time series order in a pixel-to-pixel manner (i.e., for each pixel position); and a process of generating the blood flow velocity variation information based on the plurality of pixels arranged in time series order corresponding to each pixel position. With such processing, the blood flow velocity can be determined for each position in the blood vessel region of the first cross section.

The blood flow amount calculation unit 2325 calculates the blood flow amount for each pixel through time integration of the blood flow velocity variation information for the pixel included in the blood vessel region. With this processing, the blood flow amount can be determined for each point in the blood vessel region in the first cross section.

Further, the blood flow amount calculation unit 2325 can calculate the flow amount of the blood flowing through the interested blood vessel by adding the blood flow amounts for these pixels. With this processing, the blood flow amounts for the plurality of pixels obtained in the prior stage are added together to determine the total amount of the blood that flows within the blood vessel region of the first cross section.

In the above embodiment, the optical path length difference between the optical path of the measurement light LS and the optical path of the reference light LR is changed by varying the position of the optical path length changer 41; however, a method of changing the optical path length difference is not limited to this. For example, it is possible to change the optical path length difference by providing a reflection mirror (i.e., reference mirror) in the optical path of the reference light, and moving the reference mirror in the advancing direction of the reference light to change the optical path length of the reference light. Alternatively, the optical path length difference may be changed by moving the fundus camera unit 2 and/or the OCT unit 100 with respect to the eye E to change the optical path length of the measurement light LS.

The invention claimed is:

1. A blood flow measurement apparatus comprising:
   at least one processor programmed to
      acquire an image of a living body,
      analyze the image to specify a plurality of blood vessels,
      set a plurality of measurement locations that intersect with the plurality of blood vessels before performing any scan of the living body, and
      set a single cross section that includes a plurality of cross sections of the living body corresponding to the plurality of measurement locations that intersect with the plurality of blood vessels; and
   an optical scanner configured to
      separately scan each of the plurality of cross sections of the living body corresponding to the plurality of measurement locations that intersect with the plurality of blood vessels using optical coherence tomography, and
      scan the single cross section that includes the plurality of cross sections of the living body corresponding to the plurality of measurement locations that intersect with the plurality of blood vessels using the optical coherence tomography separate from the scan of each of the plurality of cross sections, wherein
   the at least one processor is programmed to
      form a cross sectional image representing morphology in the single cross section based on data acquired from the scan of the single cross section that includes the plurality of cross sections of the living body corresponding to the plurality of measurement locations that intersect with the plurality of blood vessels, generate blood flow information on the living body based on data acquired from the separate scans of the plurality of cross sections of the living body corresponding to the plurality of measurement locations that intersect with the plurality of blood vessels, control a display device to display the cross sectional image, and control the display device to display, on the cross sectional image, blood vessel location information, indicating locations of the plurality of blood vessels at which the blood flow information is generated, based on the data acquired from the scan of the single cross section that includes the plurality of cross sections and data acquired from the separate scans of the plurality of cross sections.

2. The blood flow measurement apparatus of claim 1, wherein the at least one processor is programmed to:

calculate a width of a blood vessel in the image of the living body, and specify the plurality of blood vessels so as to include blood vessels whose width is equal to or larger than a predetermined threshold value.

3. The blood flow measurement apparatus of claim 1, wherein the processor is programmed to:

analyze the image of the living body to specify an image region corresponding to a predetermined site of the living body, and set the plurality of measurement locations in an area within a predetermined distance away from the image region.

4. The blood flow measurement apparatus of claim 1, wherein the processor is programmed to set the plurality of measurement locations so as to be orthogonal to at least part of the plurality of blood vessels.

5. The blood flow measurement apparatus of claim 1, wherein the processor is programmed to:

determine an angle formed by a blood vessel and a measurement location that intersects with the blood vessel, and correct the blood flow information based on the angle.

6. The blood flow measurement apparatus of claim 1, wherein for separately scanning each of the plurality of cross sections, the optical scanner performs a first scan that iteratively scans a first cross section and a second scan that scans a second cross section arranged close to the first cross section, for each of the plurality of cross sections, the processor is programmed to:

calculate a gradient of a blood vessel at a concerned cross section based on data acquired through the second scan, and generate the blood flow information on the blood vessel based on the gradient of the blood vessel and data acquired through the first scan.

7. The blood flow measurement apparatus of claim 6, wherein, for each of the plurality of cross sections, the processor is programmed to determine a chronological change in blood flow velocity at the concerned cross section based on the gradient of the blood vessel and the data acquired through the first scan.

8. The blood flow measurement apparatus of claim 7, wherein, for each of the plurality of cross sections, the processor is programmed to:

calculate a diameter of the blood vessel in the concerned cross section based on the data acquired through the first scan and/or the second scan, and determine a flow amount of blood flowing through the blood vessel based on the diameter of the blood vessel and the chronological change in the blood flow velocity.

9. The blood flow measurement apparatus of claim 8, wherein the processor is programmed to determine a total blood flow amount based on a plurality of flow amounts determined for the plurality of cross sections.

10. The blood flow measurement apparatus of claim 9, wherein the processor is programmed to:

determine whether a blood vessel is an artery region or a vein region, and determine a total blood flow amount for artery regions and a total blood flow amount for vein regions.

* * * * *